(12) United States Patent
Swayze et al.

(10) Patent No.: US 11,850,013 B2
(45) Date of Patent: Dec. 26, 2023

(54) SURGICAL SYSTEMS AND METHODS FOR ROBOTIC ACTUATION OF CONTINUUM JOINTS

(71) Applicant: Cilag GmbH International, Zug (CH)

(72) Inventors: Jeffrey S. Swayze, West Chester, OH (US); Andrew John Ryan, Boston, MA (US); Phillip A. Soucy, Arlington, MA (US); Carol Wood Sutherland, Somerville, MA (US)

(73) Assignee: Cilag GmbH International, Zug (CH)

( * ) Notice: Subject to any disclaimer, the term of this patent is extended or adjusted under 35 U.S.C. 154(b) by 433 days.

(21) Appl. No.: 17/233,173

(22) Filed: Apr. 16, 2021

(65) Prior Publication Data

US 2021/0322116 A1 Oct. 21, 2021

Related U.S. Application Data

(60) Provisional application No. 63/011,556, filed on Apr. 17, 2020.

(51) Int. Cl.
*A61B 34/30* (2016.01)
*A61B 34/37* (2016.01)
(Continued)

(52) U.S. Cl.
CPC .............. *A61B 34/37* (2016.02); *A61B 34/71* (2016.02); *B25J 9/102* (2013.01); *A61B 2034/301* (2016.02); *A61B 2034/305* (2016.02)

(58) Field of Classification Search
CPC ......... A61B 34/00; A61B 34/30; A61B 34/37; A61B 34/71; A61B 19/201; A61B 19/203; A61B 19/5244; A61B 2034/305
See application file for complete search history.

(56) References Cited

U.S. PATENT DOCUMENTS 5,688,270 A * 11/1997 Yates ................. A61B 18/1447
606/49
7,682,307 B2 3/2010 Danitz et al.
(Continued)

FOREIGN PATENT DOCUMENTS

WO 2009098244 A2 8/2009
WO 2009112060 A1 9/2009
(Continued)

*Primary Examiner* — Vi X Nguyen
(74) *Attorney, Agent, or Firm* — Mintz Levin Cohn Ferris Glovsky and Popeo, P.C.

(57) ABSTRACT

Robotic surgical systems are provided. In one exemplary embodiment, a robotic surgical system includes an electromechanical arm, a motor housing, a tool shaft, an end effector, and an articulation actuation system. The tool shaft includes a central body and a joint assembly having master and slave joints. The end effector is configured to move in response to movement of the slave joint. The articulation actuation system is configured to act directly on the master joint without directly acting on the slave joint to move the master joint in at least one plane. The master and slave joints are operably coupled to each other such that movement of the master joint causes parallel movement of the slave joint while maintaining a position of a longitudinal axis of the central body of the tool shaft to thereby effect articulation of the end effector. Surgical systems and methods are also provided.

12 Claims, 26 Drawing Sheets

(51) Int. Cl.
  *A61B 34/00*  (2016.01)
  *B25J 9/10*  (2006.01)

(56) References Cited

U.S. PATENT DOCUMENTS

| | | |
|---|---|---|
| 8,398,587 B2 | 3/2013 | Dewaele et al. |
| 8,740,884 B2 | 6/2014 | Verbeek |
| 8,828,046 B2 | 9/2014 | Stefanchik et al. |
| 8,986,317 B2 | 3/2015 | Verbeek |
| 9,629,689 B2 | 4/2017 | Bowles et al. |
| 9,814,451 B2 | 11/2017 | Sharma et al. |
| 9,848,858 B2 | 12/2017 | Verbeek |
| 9,869,339 B2 | 1/2018 | Zimmerman et al. |
| 2008/0004493 A1 | 1/2008 | Schiemann |
| 2008/0167670 A1* | 7/2008 | Shelton ............ A61B 17/07207 606/167 |
| 2013/0150833 A1 | 6/2013 | Peine et al. |
| 2015/0164601 A1 | 6/2015 | Sholev |
| 2017/0234411 A1 | 8/2017 | Dewaele et al. |
| 2017/0273702 A1 | 9/2017 | Dewaele et al. |
| 2018/0221045 A1 | 8/2018 | Zimmerman et al. |

FOREIGN PATENT DOCUMENTS

| | | |
|---|---|---|
| WO | 2009127236 A1 | 10/2009 |
| WO | 2017147607 A1 | 8/2017 |

* cited by examiner

SURGICAL SYSTEMS AND METHODS FOR ROBOTIC ACTUATION OF CONTINUUM JOINTS

CROSS-REFERENCE TO RELATED APPLICATIONS

This application claims priority to U.S. Provisional Patent Application No. 63/011,556, filed Apr. 17, 2020, and entitled "Steerable Wrist Actuation Methods," the disclosure of which is incorporated herein by reference in its entirety.

FIELD

Surgical systems and methods are provided for robotic actuation of one or more continuum joints of a surgical instrument.

BACKGROUND

Laparoscopic surgery is one type of minimally invasive procedure in which one or more small incisions are formed in the abdomen and a trocar is inserted through the incision to form a pathway that provides access to the abdominal cavity. The trocar can be used to introduce various instruments and tools into the abdominal cavity, as well as to provide insufflation to elevate the abdominal wall above the organs. Laparoscopic surgical devices typically include a handle, an elongate shaft, and an end effector at the distal end for effecting tissue. These devices are often preferred over traditional open surgical devices due to the reduced post-operative recovery time and minimal scarring. However, a common concern with using hand held laparoscopic devices is reduced dexterity, which can act as a barrier to performing laparoscopic surgery as a less invasive alternative to open surgery.

To enhance dexterity, laparoscopic surgical devices with an articulating end effectors have been developed. Some of these devices employ one or more cables that extend through guide sleeve(s) within the shaft and directly act on the distal end of the shaft to thereby articulate the end effector. The incorporation of the one or more cables and guide sleeve(s), however, can result in a bulkier shaft. Other devices are designed with one or more continuum joints (e.g., a joint that has continuous flexion over a length of the joint as compared to a joint with discrete axis/pivot points). However, the architecture of these continuum joints is typically designed to be used in hand held laparoscopic surgical devices. As a result, the actuation mechanisms can create significant challenges for use with traditional robotic actuation methods.

Accordingly, there remains a need for improved systems that address current issues with robotic actuation of laparoscopic surgical devices.

SUMMARY

Robotic surgical systems are provided. In one exemplary embodiment, a robotic surgical system includes an electromechanical arm, a motor housing configured to be mounted to the electromechanical arm, a tool shaft extending from the motor housing, an end effector, and an articulation actuation system. The motor housing has at least one motor disposed therein. The tool shaft includes a central body and a joint assembly. The central body has a proximal-most end, a distal-most end, and a longitudinal axis extending therebetween. The joint assembly has a master joint coupled to the proximal-most end of the central body and a slave joint coupled to the distal-most end of the central body. The end effector is coupled to a distal-most end of the slave joint, and the end effector is configured to move in response to movement of the slave joint. The articulation actuation system is coupled to the master joint and configured to act directly on the master joint without directly acting on the slave joint to move the master joint in at least one plane. The master and slave joints are operably coupled to each other such that movement of the master joint causes parallel movement of the slave joint while maintaining a position of the longitudinal axis of the central body of the tool shaft to thereby effect articulation of the end effector in at least one plane about the central body of the tool shaft.

The master and slave joints can have a variety of configurations. In some embodiments, the master joint and the slave joint can each be a continuum joint.

The tool shaft can have a variety of configurations. In some embodiments, the tool shaft can include circumferentially spaced flexible tendons. The flexible tendons can longitudinally extend along a length of the tool shaft, in which the length can extend from a proximal-most end of the master joint to the distal-most end of the slave joint. The central body of the tool shaft can include a portion of each flexible spline, in which the portion can extend between the master and slave joints.

In some embodiments, the system can include a shaft roll actuation system that can be coupled to the tool shaft and can be configured to rotate the tool shaft relative to the motor housing and the electromechanical arm.

In some embodiments, the system can include an instrument roll actuation system that can be coupled to the motor housing and can be configured to rotate the tool shaft and a motor chassis within the motor housing simultaneously relative to the electromechanical arm.

In some embodiments, movement in the at least one plane can be at least one of pitch and yaw. In other embodiments, movement of the master joint in a first plane of the at least one plane can be pitch and movement of the master joint in a second plane of the at least one plane can be yaw.

The articulation actuation system can have a variety of configurations. In some embodiments, the articulation actuation system can include a plurality of lever arms positioned at the proximal end of the master joint, in which each lever arm can be configured to move the master joint in a respective one direction within the at least one plane. In such embodiments, the articulation actuation system can include a plurality of cables, in which each cable can extend from a respective lever arm to a respective motor of the at least one motor, and the respective motor can be configured to tension the respective cable, and the respective motor can be configured to further pull the respective tension cable to thereby cause movement of the respective lever. In certain embodiments, the articulation actuation system can include at least one gear that can be operatively coupled to the master joint and can be configured to control movement of the master joint. In one embodiment, the articulation actuation system can include at least one pulley assembly that can have at least one pulley and respective cable, in which the at least one pulley assembly can be configured to cause rotation of the at least one gear to thereby cause articulation of the master joint in the at least one plane. In another embodiment, the articulation actuation system can include at least one lead screw that can be coupled to the at least one gear and can be configured to cause rotational movement of the at least one gear to thereby cause articulation of the master joint in the at least one direction.

The motor housing can have a variety of configurations. In some embodiments, the motor housing can be configured to be removably coupled to the electromechanical arm.

Surgical systems are also provided. In one exemplary embodiment, a surgical system includes a surgical instrument that is configured to be removably coupled to an electromechanical arm of a robotic system. The surgical instrument includes a tool shaft assembly having a central shaft, a first continuum joint, a second continuum joint, an end effector, and an articulation coupler. The central shaft has a distal-most end, a proximal-most end, and a longitudinal axis extending therebetween. The first continuum joint is coupled to the proximal-most end of the central shaft, and the second continuum joint is coupled to the distal-most end of the central shaft. The end effector is coupled to a distal-most end of the second continuum joint, in which the combination of the first and second continuum joints are configured to cause movement of the end effector. The articulation coupler is directly coupled to the first continuum joint and is configured to articulate the first continuum joint relative to the longitudinal axis of the central shaft, in which the articulation coupler is configured to be operably coupled to a robotic surgical system. The first continuum joint is operatively associated with the second continuum joint such that the articulation of the first continuum joint in a first direction causes articulation of the second continuum joint relative to the longitudinal axis of the central shaft in a second direction to thereby allow the end effector to pitch relative to the longitudinal axis of the central shaft, in which the second direction being opposite the first direction.

In some embodiments, the surgical instrument can include a stage that can be configured to be removably coupled to a motor housing on the electromechanical arm, in which the tool shaft assembly can be configured to mate to the electromechanical arm through the stage. In one embodiment, the tool shaft assembly can be removably coupled to the stage. In another embodiment, the tool shaft assembly can be permanently coupled to the stage.

In some embodiments, the surgical instrument can include an articulation actuation system that can be directly coupled to the articulation coupler and can be configured to articulate the articulation coupler to thereby cause articulation of the first continuum joint. The articulation actuation system can include at least one articulation rack and at least one gear that can be engaged with the at least one articulation rack, in which the at least one articulation rack can be configured to axially translate so as to rotate the at least one gear to thereby cause articulation of the articulation coupler. The articulation actuation system can include a pulley assembly that can be coupled to the articulation rack and can be configured to axially translate the articulation rack.

In some embodiments, the system can include the electromechanical arm, a motor housing configured to be mounted to the electromechanical arm, and a shaft roll actuation system. The motor housing can have at least one motor disposed therein. The shaft roll actuation system can be coupled to the central shaft and can be configured to rotate the central shaft and the first and second continuum joints relative to the motor housing and the electromechanical arm.

In some embodiments, the system can include the electromechanical arm, a motor housing that can be configured to be mounted to the electromechanical arm, and an instrument roll actuation system. The motor housing can have a motor chassis disposed therein, in which the motor chassis can have at least one motor coupled thereto. The instrument roll actuation system that can be coupled to motor housing and can be configured to rotate the tool shaft assembly and the motor chassis simultaneously relative to the electromechanical arm.

Surgical methods are also included. In one exemplary embodiment, the method includes directing a surgical instrument coupled to an electromechanical arm to a surgical site, the instrument having a tool shaft, an end effector at a distal end of the tool shaft, and an articulation coupler, the tool shaft having a central body with a proximal continuum joint coupled to a proximal-most end of the central body and a distal continuum joint coupled to a distal-most end of the central body, the central body having a longitudinal axis that extends between the proximal-most end and the distal-most end, the articulation coupler being coupled to the proximal continuum joint and configured to directly articulate the proximal continuum joint relative to the longitudinal axis of the central body. The method also includes actuating the articulation coupler to directly articulate the proximal continuum joint to cause parallel motion of the distal continuum joint while the longitudinal axis of the central body remains static to thereby cause articulation of the end effector in at least one plane about the central body of the tool shaft.

In some embodiments, actuation of the articulation coupler cannot cause direct articulation of the distal continuum joint.

In some embodiments, the method includes rotating at least one of the surgical instrument and the tool shaft to thereby cause rotation of the end effector.

In some embodiments, actuating the articulation coupler can include actuating an articulation actuation system that can be coupled to the articulation coupler to cause the proximal continuum joint to at least one of pitch and yaw relative to the longitudinal axis of the central body of the tool shaft. In such embodiments, the articulation actuation system can include an articulation rack, at least one gear that can be engaged with the articulation rack, and a pulley assembly that can be coupled to the articulation rack, in which actuating the articulation actuation system can include actuating the pulley assembly to cause axial translation of the articulation rack so as to rotate the at least one gear. The at least one gear can be coupled to the articulation coupler such that rotation of the at least one gear causes the proximal continuum joint to pitch.

BRIEF DESCRIPTION OF THE DRAWINGS

This invention will be more fully understood from the following detailed description taken in conjunction with the accompanying drawings, in which.

DETAILED DESCRIPTION

Figure 1:
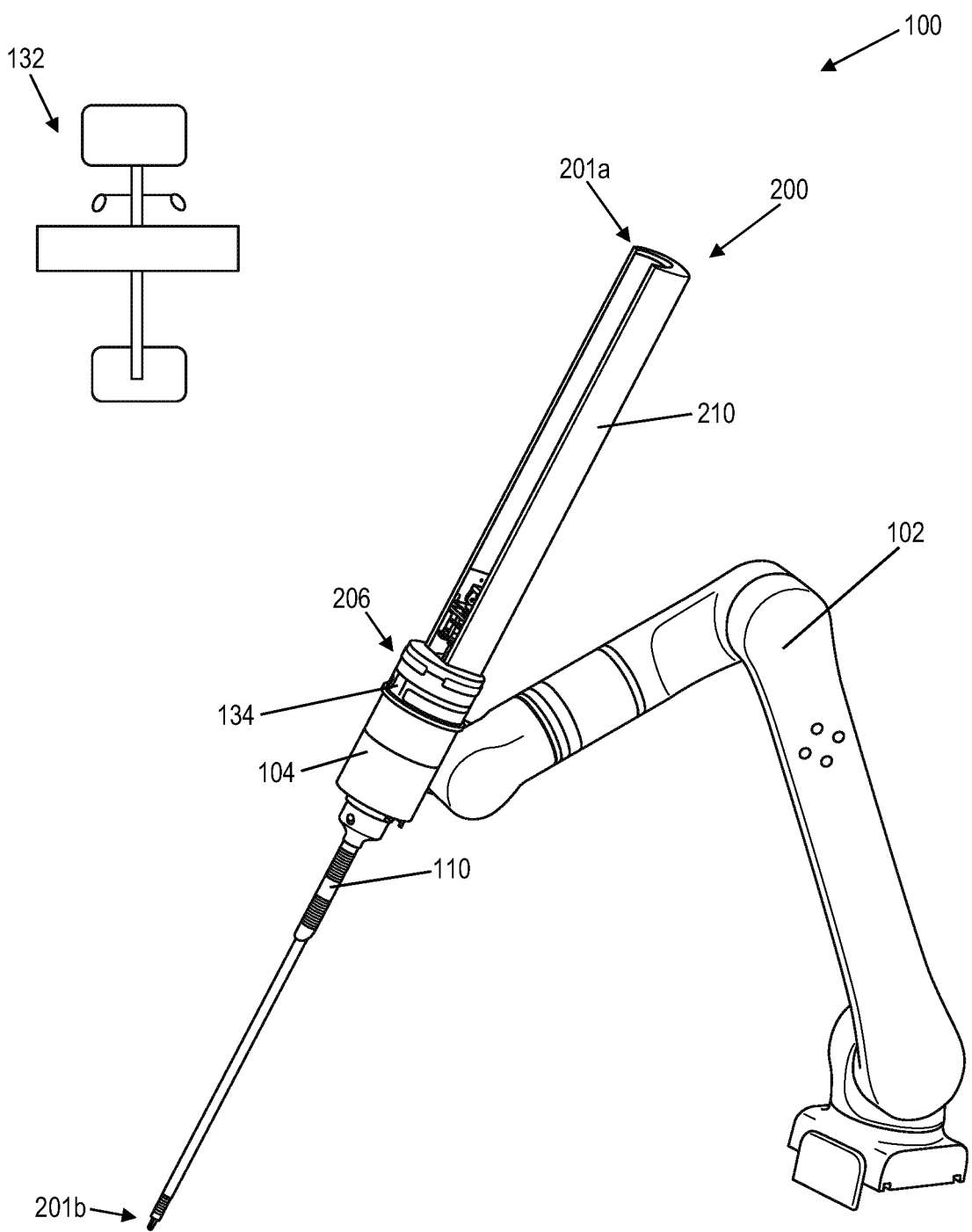
FIG. 1 is a perspective view of an exemplary embodiment of a surgical robotic system that includes an electromechanical arm having a motor housing and an exemplary surgical instrument mounted thereto, and being wirelessly coupled to a control system.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, the present invention relates to a surgical system having a surgical instrument that includes an articulation actuation system and a joint assembly. As discussed in greater detail below, the surgical instrument can be configured to be coupled to an electromechanical arm of a robotic system. In certain exemplary aspects, the joint assembly can include a master joint and a slave joint (e.g., each being a continuum joint, e.g., joints that have continuous flexion along a length of the joint as compared to joints with discrete axis/pivot points) that are configured to articulate an end effector that is coupled to the slave joint. The articulation actuation system is coupled to the master joint and configured to act directly on the master joint without directly acting on the slave joint to thereby move the master joint in at least one plane. The master and slave joints are operably coupled to each other such that movement of the master joint causes parallel movement of the slave joint to thereby effect articulation of the end effector. That is, articulation of the end effector occurs by directly manipulating only the master joint (e.g., by the articulation actuation system). As a result, unlike conventional instruments (e.g., instruments that require direct manipulation of the slave joint), the present surgical instruments are designed to effect articulation of the end effector without directly acting on the slave joint.

An exemplary surgical instrument can include a variety of features as described herein and illustrated in the drawings. However, a person skilled in the art will appreciate that the surgical instruments can include only some of these features and/or it can include a variety of other features known in the art. The surgical instruments described herein are merely intended to represent certain exemplary embodiments. Moreover, while the surgical instruments are shown and described in connection with tool shafts having a jaw assembly at a distal end thereof, a person skilled in the art will appreciate that these instruments can be used in connection with tool shafts having other types of end effectors, such as needle drivers, scissors, staplers, electrocautery tools, clip appliers/removers, etc. Further, while the surgical instruments are shown and described in connection with master and slave continuum joints, a person skilled in the art will appreciate that these instruments can be used with other types of master and slave joints, such as those utilizing spherical (ball and socket) joints or revolute joints.

Figure 2:
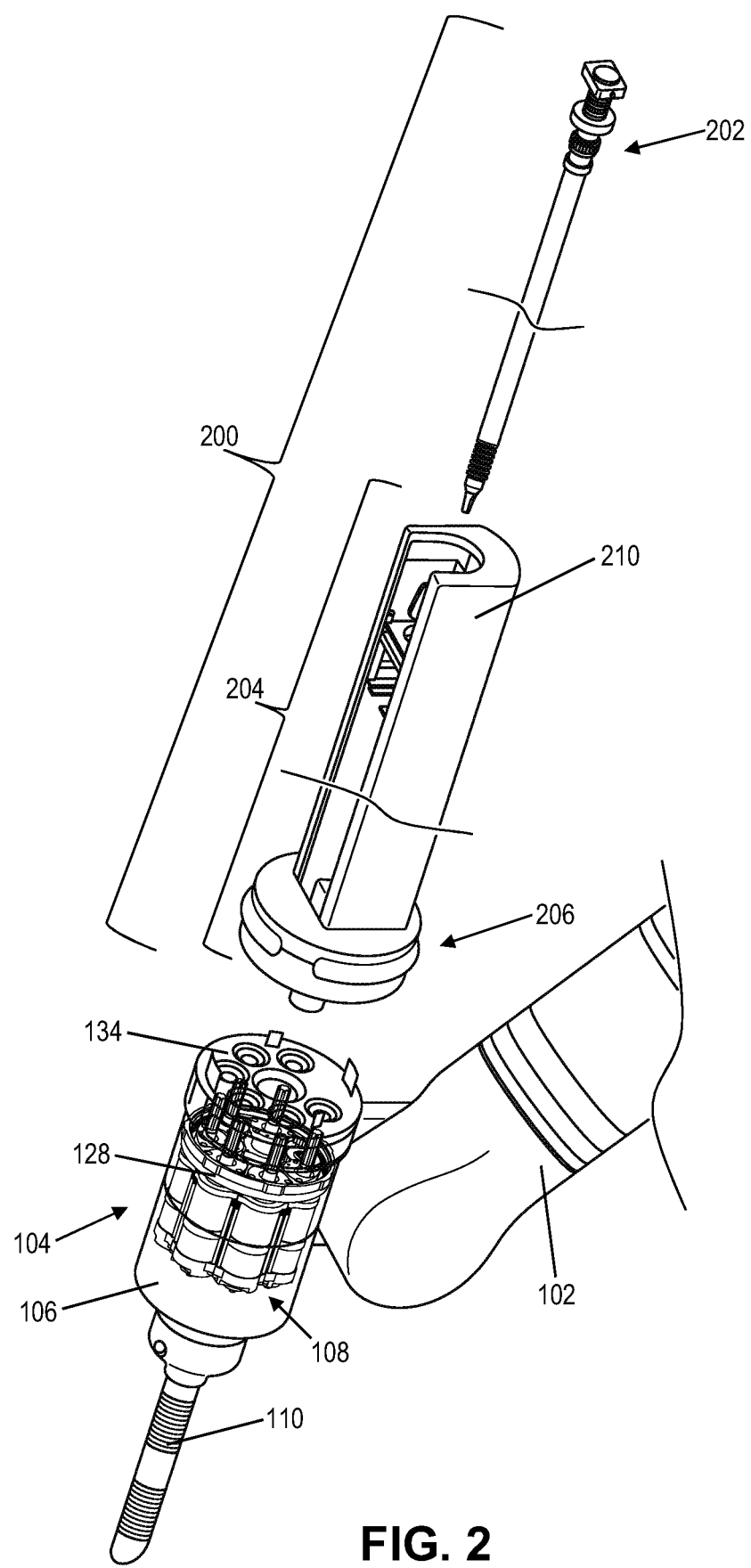
FIG. 2 is a partial exploded view of the surgical instrument of FIG. 1 relative to the electromechanical arm and motor housing coupled thereto.
Figure 3:
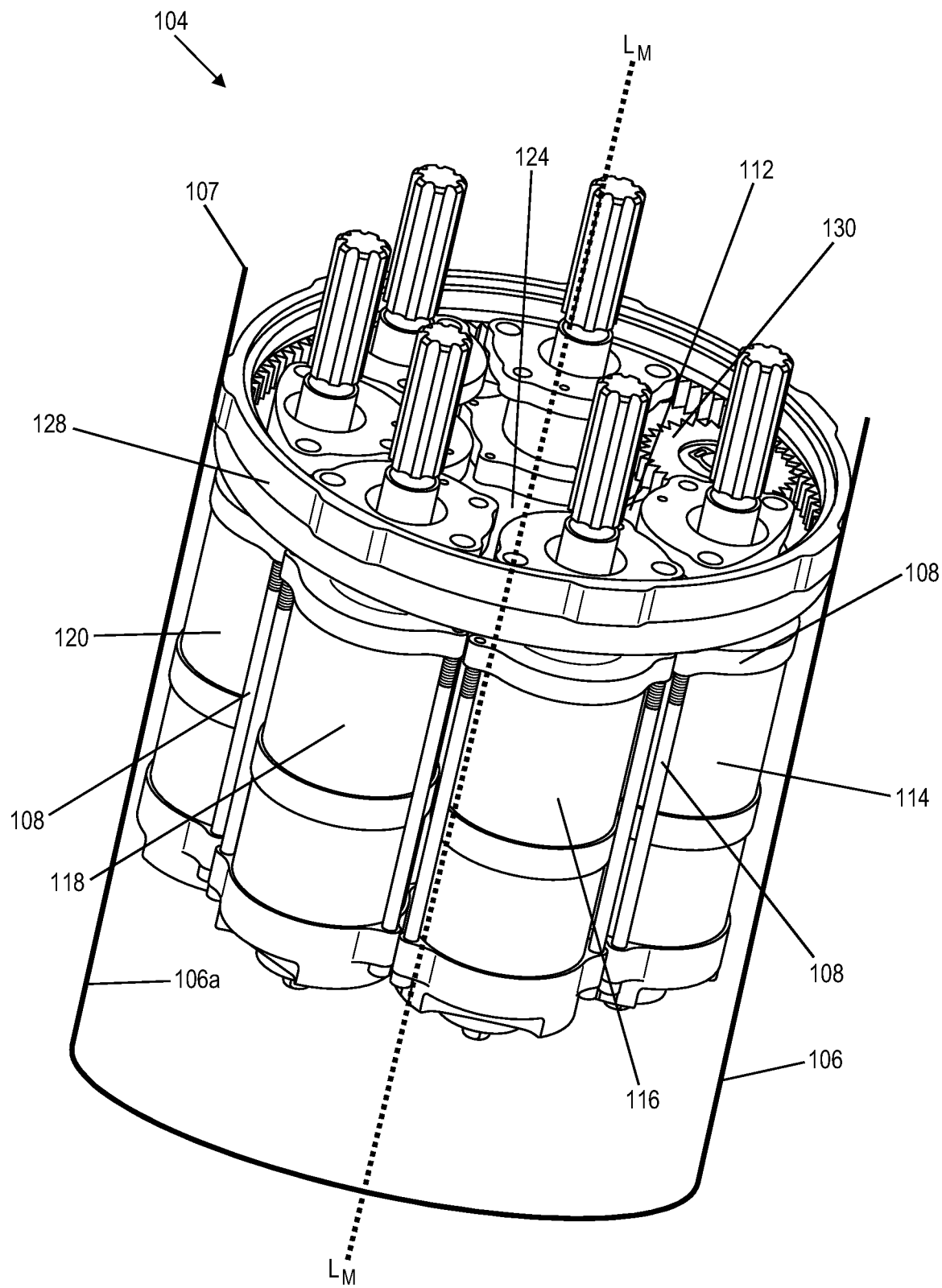
FIG. 3 is a magnified view of a portion of the motor housing.

FIGS. 1 and 2 illustrate an exemplary robotic surgical system 100 having an electromechanical arm 102 and a motor housing 104 that is mounted to the electromechanical arm 102. The motor housing 104, as shown in FIG. 3, includes an outer sleeve 106 and a motor chassis 108 disposed within the outer sleeve 106. The motor chassis 108 includes one or more motors coupled thereto. As will be described in more detail below, in this illustrated embodiment, the motor housing 104 includes seven motors (first motor 112, second motor 114, third motor 116, fourth motor 118, fifth motor 120, sixth motor 122 (obstructed), seventh motor 124). The motors are operably coupled to and configured to actuate one or more actuation systems (e.g., instrument roll actuation system, shuttle translation actuation system, articulation actuation system, shaft roll actuation system, and jaw actuation system). As further shown, an exemplary surgical instrument 200 is removably mounted to the motor housing 104, and thus to the electromechanical arm 102.

The motor housing 104, as shown in more detail in FIG. 3, includes an instrument roll actuation system that is configured to rotate the motor chassis 108 about the longitudinal axis $L_M$ of the motor housing 104 and relative to the outer sleeve 106, and thus, relative to the electromechanical arm 102. In use, since the surgical instrument 200 is mounted to the motor housing 104 and coupled to the motor chassis 108, rotation of the motor chassis 108 also causes rotation of the surgical instrument 200 about the longitudinal axis $L_M$ of the motor housing 104.

The instrument roll actuation system can have a variety of configurations. In this illustrated embodiment, the instrument roll actuation system includes a ring gear 128 and a pinion gear 130 that are configured to engage with each other. The ring gear 128 is mounted to an internal surface 106a of the outer sleeve 106 and positioned proximate to the top end 107 of the outer sleeve 106, and therefore, the ring gear 128 remains stationary relative to the pinion gear 130. The pinion gear 130 is operably coupled to the first motor 112 (e.g., the instrument roll motor). As a result, actuation of the first motor 112 causes the pinion gear 130 to rotate and travel along the ring gear 128. This rotation of the pinion gear 130 drives the rotation of the motor chassis 108 and the surgical instrument 200 about the longitudinal axis $L_M$ of the motor housing 104 relative to the electromechanical arm 102.

The electromechanical arm 102 can be wirelessly coupled to a control system 132. In other embodiments, the electromechanical arm 102 can be wired to the control system 132. While the control system 132 can have a variety of configurations, in this illustrated embodiment, the control system 132 has a console with a display and two user input devices. Further, the control system 132 can include component(s) of a computer-based control system that stores computer program instructions, for example, within a non-transitory computer-readable storage medium such as a persistent magnetic storage drive, solid state drive, etc. The execution of those instructions can control the entire system or sub-system(s) thereof. For example, when executed by a processor of the computer system, the instructions can cause the components of the robotic surgical system to actuate any electromechanical arm thereof and/or control any surgical instrument coupled thereto.

The surgical instrument 200 extends from a proximal end 201a to a distal end 201b. The surgical instrument 200 includes a tool shaft assembly 202 and a stage 204. In use, as shown in FIG. 1, at least a portion of the tool shaft assembly 202 is inserted into and extends through the motor housing 104 and a trocar 110 coupled to the motor housing 104. In this illustrated embodiment, the tool shaft assembly 202 and the stage 204 are configured to be removably coupled to each other, and therefore, during use, they can be independently replaced if needed. In other embodiments, the tool shaft assembly 202 can be permanently mounted to the stage 204. Further, as shown, the stage 204 is configured to be removably coupled to the motor housing 104 mounted on the electromechanical arm 102, and thus, the tool shaft assembly 202 is configured to mate to the electromechanical arm 102 through the stage 204 and motor housing 104. In certain embodiments, as shown in FIGS. 1-3, the motor housing 104 can include a sterile adapter 134 that is coupled to the motor housing 104 and that is positioned between the motor housing 104 and the stage 204 of the surgical instrument 200. In other embodiments, the sterile adapter 134 can be omitted.

Figure 4:
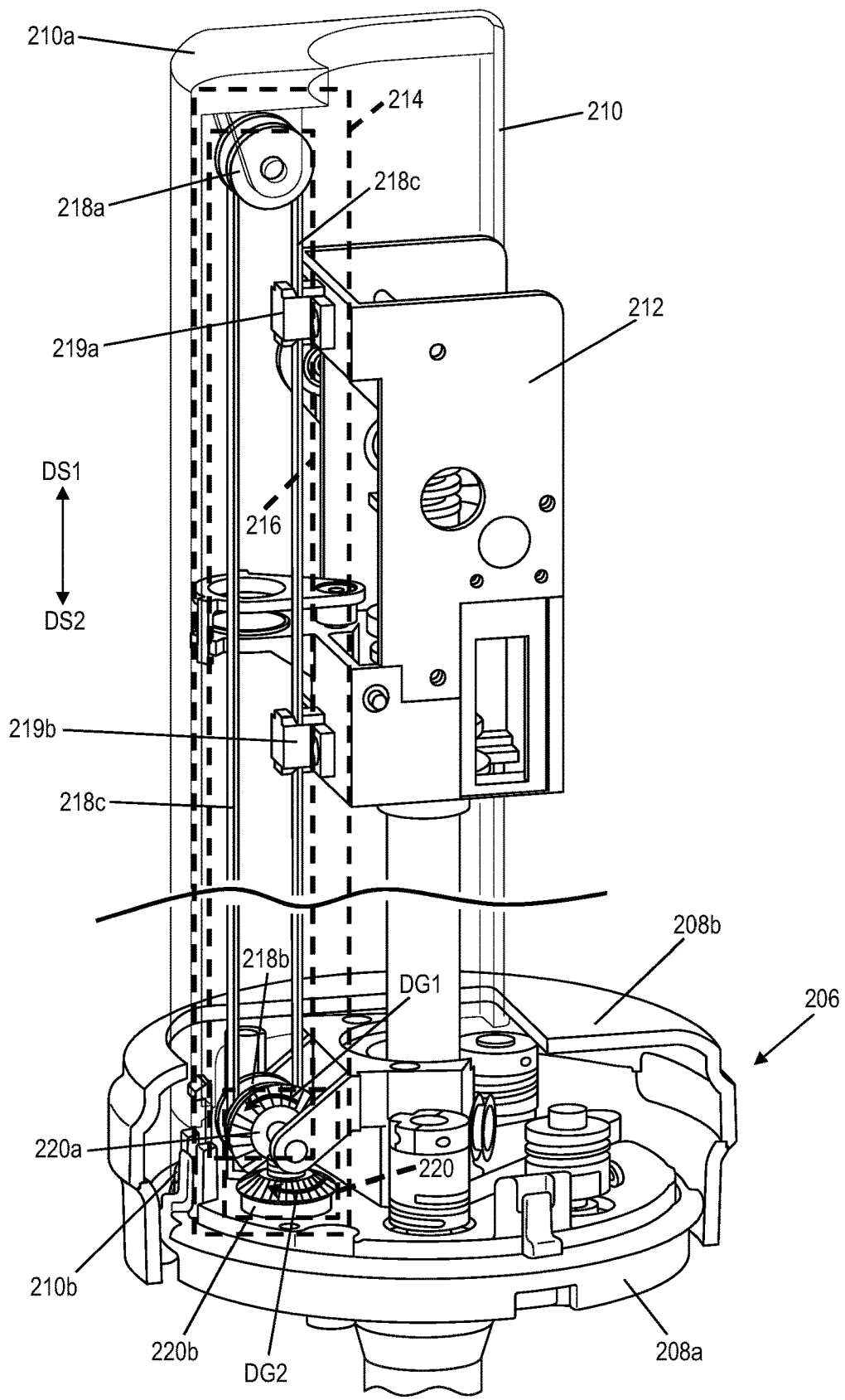
FIG. 4 is a side perspective cut-away view of a portion of the surgical instrument of FIG. 2.

While the stage can have a variety of configurations, the stage 204 includes a base 206 and a carriage 210 that is coupled to and extends from the base 206. The base 206 has a generally cylindrical shape and is formed of a base plate 208a (see FIGS. 7-8) and a cover 208b. In use, as shown in FIG. 1, the base 206 is coupled to the motor housing 104. While the carriage 210 can have a variety of different configurations, in this illustrated embodiment, the carriage 210 has a generally u-shaped configuration and extends from a top end 210a to a bottom end 210b. The bottom end 210b is coupled to the base plate 208a of the base 206, as shown in FIG. 4. As will be discussed in more detail, the carriage 210 is configured to house a shuttle 212 and components of various actuation systems of the surgical instrument 200, such as articulation actuation system 238 and shaft roll actuation system 260, to effect articulation and rotation of the tool shaft assembly 202.

In certain embodiments, the shuttle 212 can be configured to axially translate through the carriage 210. In this illustrated embodiment, the shuttle 212 is translated by actuation of a shuttle translation actuation system 214, which is shown in more detail in FIG. 4. The shuttle translation actuation system 214 includes a first pulley assembly 216 having a first pulley 218a positioned at or proximate to the top end 210a of the carriage 210 and a second pulley 218b that is coupled to the base plate 208a of the base 206. The first pulley assembly further includes a belt 218c that is looped about the first and second pulleys 218a, 218b and is clamped to the shuttle 212 via first and second belt clamps 219a, 219b. The shuttle translation actuation system 214 also includes a gear assembly 220 that is coupled to and configured to actuate the first pulley assembly 216 to thereby cause the shuttle 212 to axially translate within the carriage 210. The gear assembly 220 includes first and second beveled gears 220a, 220b that are engaged to each other, in which the first bevel gear 220a is coupled to the second pulley 218b and the second bevel gear 220b is operably coupled to the fourth motor 118 within the motor housing 104.

In use, rotation of the second bevel gear 220a via the fourth motor 118 in a first direction DG1 (see FIG. 4, e.g., in a clockwise (CW) direction) causes the first bevel gear 220a to rotate in a second direction DG2 (see FIG. 4, e.g., in a counter-clockwise (CCW) direction). This rotation of the first bevel gear 220a causes the second pulley 218b to rotate. Given the engagement (e.g., frictional or mechanical) that exists between the second pulley 218b and the belt 218c, the rotation of the second pulley 218b drives the belt 218c such that the shuttle 212 axially translates along the carriage 210 in a first direction DS1 (see FIG. 4, e.g., in a direction toward the top end 210a of the carriage 210). Similarly, rotation of the second bevel gear 220b in a third direction (e.g., CCW direction) causes the first bevel gear 220a to rotate in a fourth direction (e.g., CW direction), and ultimately, drives the belts 218c such that the shuttle 212 axially translates along the carriage 210 in a second direction DS2

(see FIG. 4, e.g., in a direction toward the base 206). In certain embodiments, the axial translation of the shuttle 212 can also be used to axially translate the tool shaft assembly 202 relative to the motor housing 104 such that the distal end of the tool shaft assembly 202 (e.g., the end effector 228) can be inserted into and removed from a patient in a more controlled manner.

Figure 5:
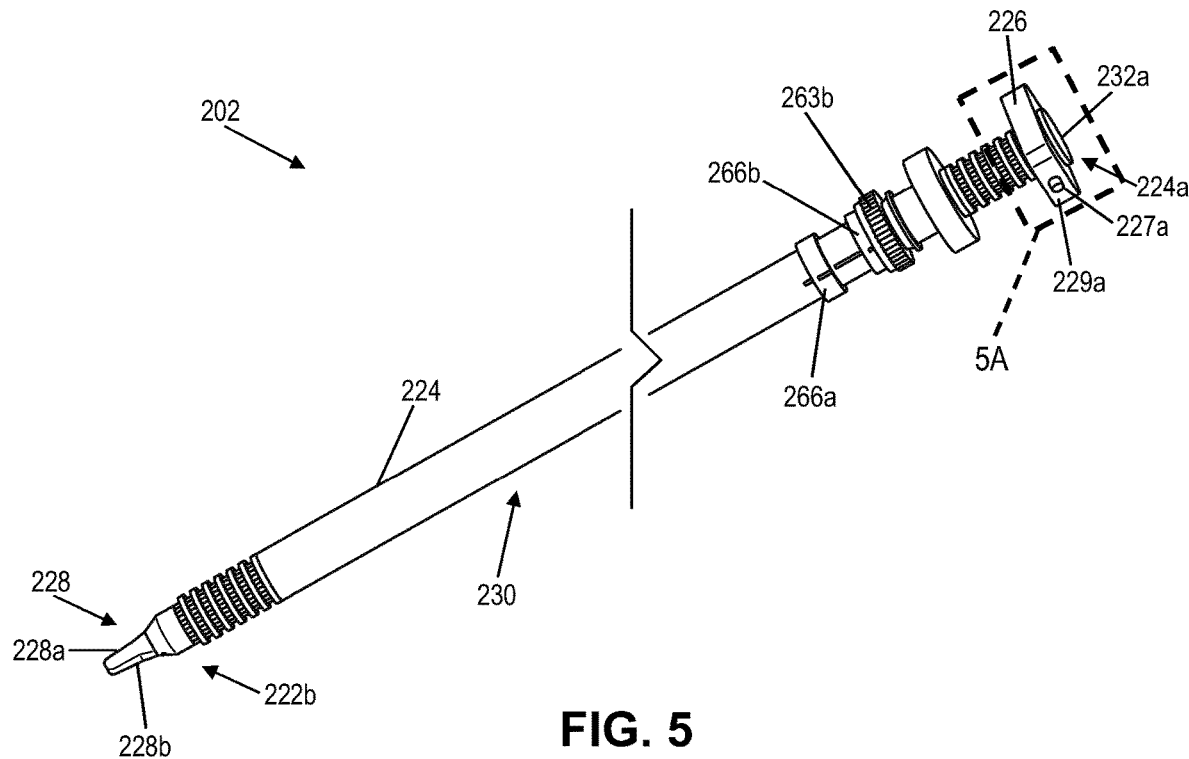
FIG. 5 is a perspective view of a tool shaft assembly of the surgical instrument of FIG. 1, the tool shaft assembly having a tool shaft, an outer sleeve about a portion of the tool shaft, an end effector coupled to a distal end of the tool shaft, and an articulation coupler coupled to a proximal end of the tool shaft.
Figure 6:
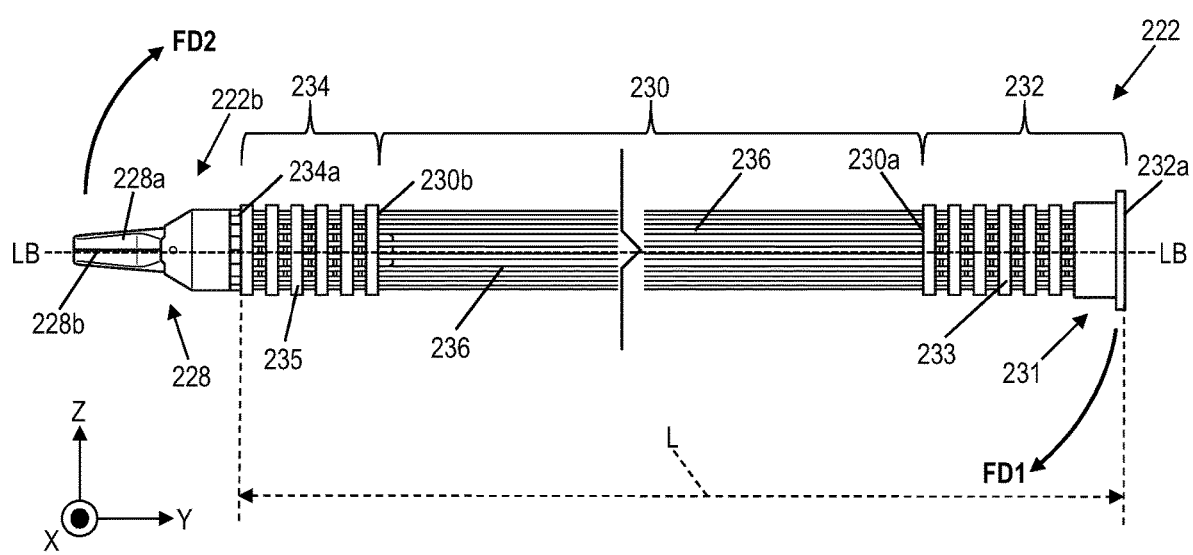
FIG. 6 is a side view of the tool shaft and end effector of FIG. 5.

As shown in more detail in FIGS. 5 and 6, the tool shaft assembly 202 includes a tool shaft 222, an outer sleeve 224 that extends about a portion of the tool shaft 222, an articulation coupler 226 positioned at the proximal end 224a of the tool shaft 222, and an end effector 228 positioned at the distal end 222b of tool shaft 222. While any suitable end effector can be coupled to the tool shaft 222, in this illustrated embodiment, the end effector 228 includes two opposing jaws 228a, 228b pivotally coupled to each other and configured to move between open and closed positions. The tool shaft assembly 202 also includes a shaft gear 263b, which is part of the shaft roll actuation system 260, and first and second jaw coupling rings 266a, 266b, which is part of the jaw actuation system 264, as will be discussed in more detail below. Further, while the tool shaft assembly 202 is illustrated as having an outer sleeve 224, in certain embodiments, the outer sleeve 224 can be omitted.

The tool shaft 222, which is shown in more detail in FIG. 6, includes a central body or central shaft 230 that has a proximal-most end 230a, a distal-most end 230b, and a longitudinal axis LB extending therebetween. The tool shaft 222 also includes a master or first continuum joint 232 that is coupled to the proximal-most end 230a of the central body 230 and a slave or second continuum joint 234 that is coupled to the distal-most end 230b of the central body 230. The master and slave continuum joints 232, 234 are collectively referred to herein as a joint assembly. As shown, the master continuum joint 232 includes first interconnected disks 233 and the slave continuum joint 234 includes second interconnected disks 235. As shown, the end effector 228 is coupled to the distal-most end 234a of the slave continuum joint 234. The master and slave continuum joints 232, 234 are configured to be operably coupled to each other such that movement of the master continuum joint 232 causes parallel movement of the slave continuum joint 234 while maintaining a position of the longitudinal axis LB of the central body 230 of the tool shaft 22. This parallel movement effects articulation of the end effector 228 in at least one plane about the central body 230 of the tool shaft 222.

In some embodiments, the at least one plane is at least one of pitch (e.g., movement about the X-axis in the YZ plane) and yaw (e.g., movement in the about the Z-axis in the XY plane). For example, in certain embodiments, movement of the master continuum joint 232 in a first plane (e.g., in the YZ plane) of the at least one plane is pitch. Alternatively, or in addition, movement of the master continuum joint 232 in a second plane (e.g., XY plane) of the at least one plane is yaw.

As further shown in FIG. 6, the tool shaft 222 includes circumferentially spaced flexible tendons 236 that longitudinally extend along a length L of the tool shaft 222. As shown, the length L of the tool shaft 222 extends from the proximal-most end 232a of the master continuum joint 232 to the distal-most end 234a of the slave continuum joint 234. Further, the central body includes the portion of each of the flexible tendons 236 that extend between the master and slave continuum joints 232, 234. As a result, the master continuum joint 232 is operably coupled to the slave continuum joint 234 via the flexible tendons 236, and during use, the movement of the master continuum joint 232 transitions to the slave continuum joint 234 through the flexible tendons 236. The resulting parallel movement between the master and slave continuum joints 232, 234 therefore occurs relative to the static longitudinal axis LB of the central body 230 of the tool shaft 222.

By way of example, during use, articulation of the master continuum joint 232 in a first direction FD1 (see FIG. 6) relative to the longitudinal axis LB of the central body 230 causes articulation of the slave continuum joint relative 234 relative to the longitudinal axis LB of the central body 230 in a second direction FD2 (see FIG. 6) that is opposite to the first direction FD1. This results in parallel movement between the master and slave continuum joints 232, 234. In this example, the articulation of the master continuum joint 232 in the first direction FD1 and the slave continuum joint 234 in the second direction FD2 causes the end effector 228 to pitch (e.g., rotate about the X-axis in the YZ plane) relative to the longitudinal axis LB of the central body. As such, since the end effector 228 is directly coupled to the slave continuum joint, the articulation direction of the end effector 228 corresponds to the articulation direction of the slave continuum joint 234. Additional details on exemplary tool shafts with continuum joints can be found in U.S. Pat. Nos. 8,398,587, 8,740,884, 8,986,317, and 9,848,858, and U.S. Patent Publication Nos. 20170234411 and 20170273702, each of which is incorporated herein by reference in its entirety.

Figure 5A:
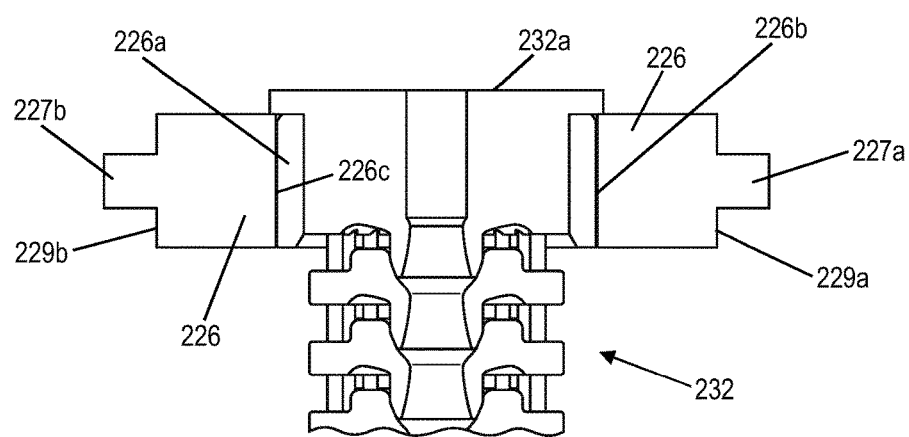
FIG. 5A is a cross-sectional magnified side view of a portion of the tool shaft assembly of FIG. 5 taken at 5A.

Referring back to FIG. 5, the articulation coupler 226 is directly coupled to the master continuum joint 234 and is configured to articulate the master continuum joint 234 relative to the longitudinal axis LB of the central body 230 of the tool shaft 222. While the articulation coupler 226 can have a variety of structural configurations, in this illustrated embodiment, the articulation coupler 226 has a base member 226a with a central channel 226b extending therethrough. The base member 226a can have any suitable shape. As shown, the base member 226a has a generally rectangular structural configuration. The central channel 226b is shaped complementary to a proximal portion 231 (see FIG. 6) of the master continuum joint 232 such that the articulation coupler 226 can be coupled to the master continuum joint 232 proximate and adjacent to the proximal-most end 232a of the master continuum joint 232. Further, as shown in FIG. 5A, a bushing 225 is positioned between the master continuum joint 232 and the inner surface 226c of the central channel 226 to thereby allow the tool shaft 222 to rotate relative to the articulation coupler 226. While the bushing 225 can have a variety of configurations, in this illustrated embodiment, the bushing 225 has a generally barrel shape. In other embodiments, the bushing 225 can be replaced with a bearing or any other suitable element that can be configured to allow the tool shaft 222 to rotate relative to the articulation coupler 226.

Figure 7:
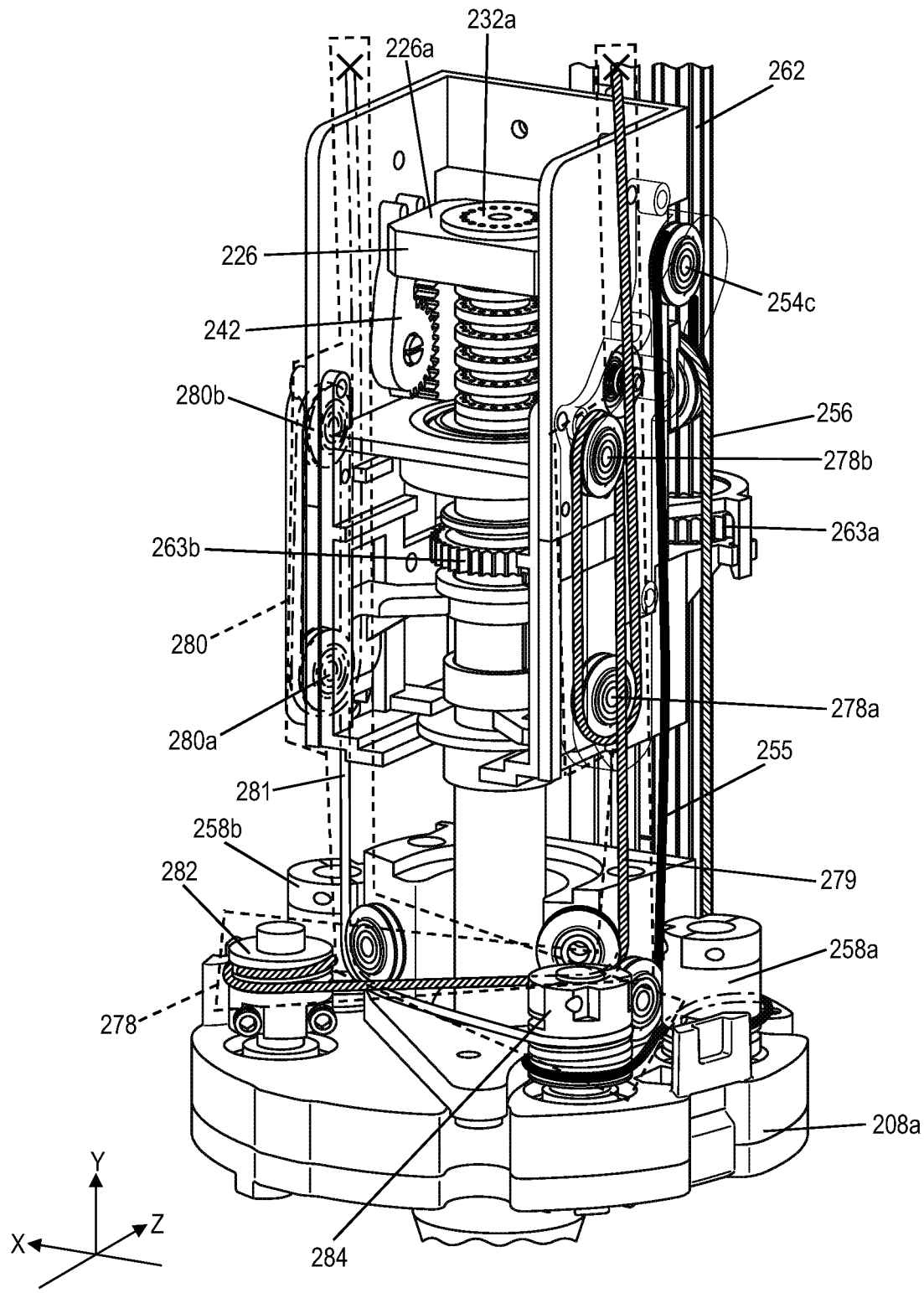
FIG. 7 is a front perspective view of a portion of the surgical instrument of FIG. 1 with certain components thereof removed.
Figure 9:
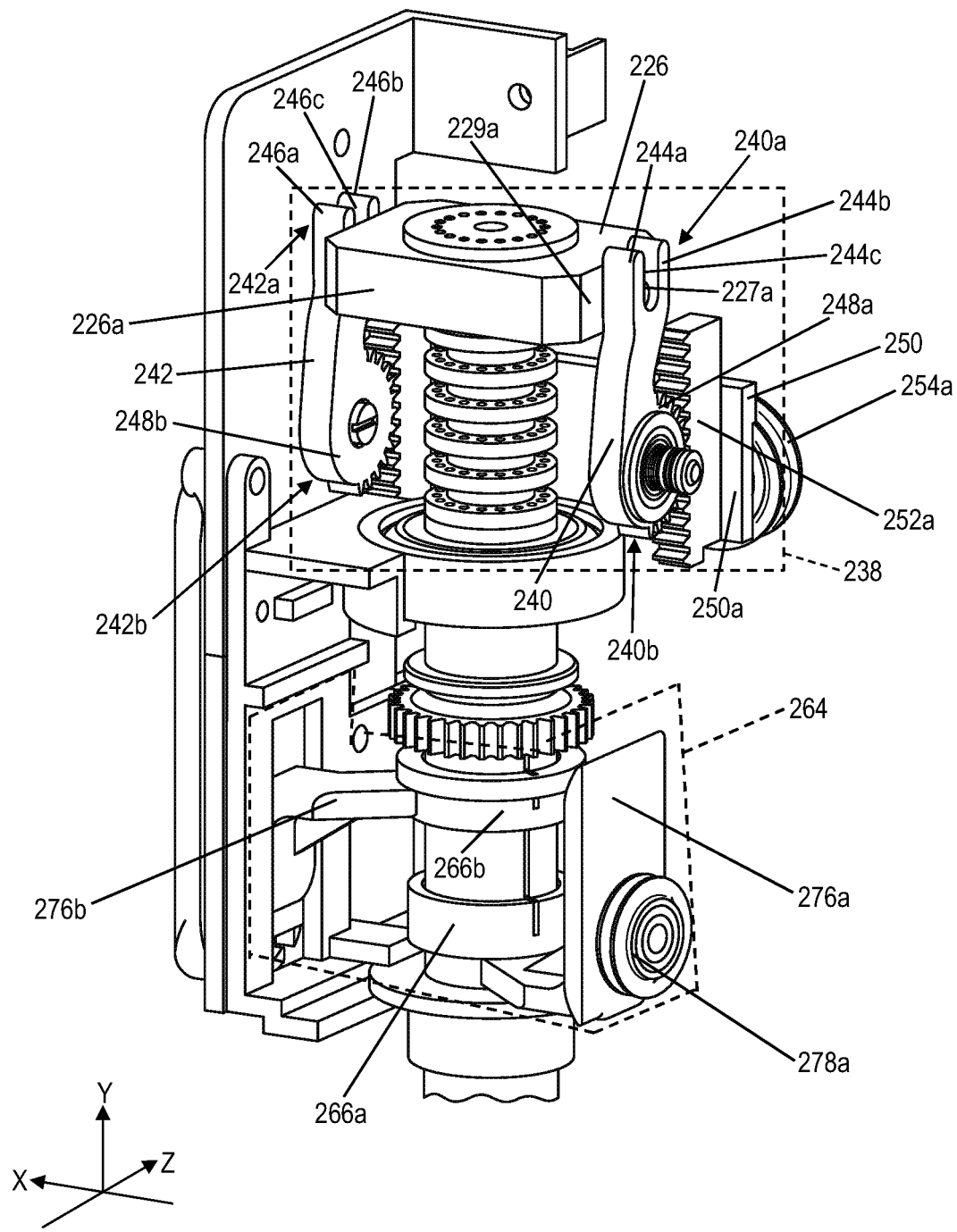
FIG. 9 is magnified view of a portion of the surgical instrument of FIG. 7 with certain components removed.

Further, the articulation coupler 226 is configured to couple to an articulation actuation system 238 of the surgical instrument 200. For example, in this illustrated embodiment, as shown in more detail in FIG. 5A, the articulation coupler 226 includes two opposing side posts (first side post 227a and second side post 227b) that extend from respective opposite sides (first side 229a and second side 229b) of the base member 226a. These first and second side posts 227a, 227b are configured to couple the tool shaft 222 to the articulation actuation system 238 of the surgical instrument 200, as shown in FIGS. 7 and 9. A person skilled in the art will appreciate that the structural configuration of the articulation coupler and the engagement of the articulation coupler to the articulation actuation system depends at least upon the structural configuration of the tool shaft and the coupling interface of the articulation actuation system, and therefore the articulation coupler is not limited to the structural configuration and engagement that is illustrated in the figures. In certain embodiments, a retention clip can be used to prevent axial movement of the tool shaft 222 relative to the shuttle 212.

As discussed above, the surgical instrument 200 includes an articulation actuation system that is coupled to the master continuum joint and configured to act directly on the master continuum joint without directly acting on the slave continuum joint to move the master continuum joint in at least one plane. As such, the slave continuum joint is not directly articulated via the articulation activation system. That is, during use, the articulation actuation system only directly controls the articulation of the master continuum joint, and the articulation of the master continuum joint is transitioned along the flexible tendons to cause parallel movement of the slave continuum joint.

Figure 10A:
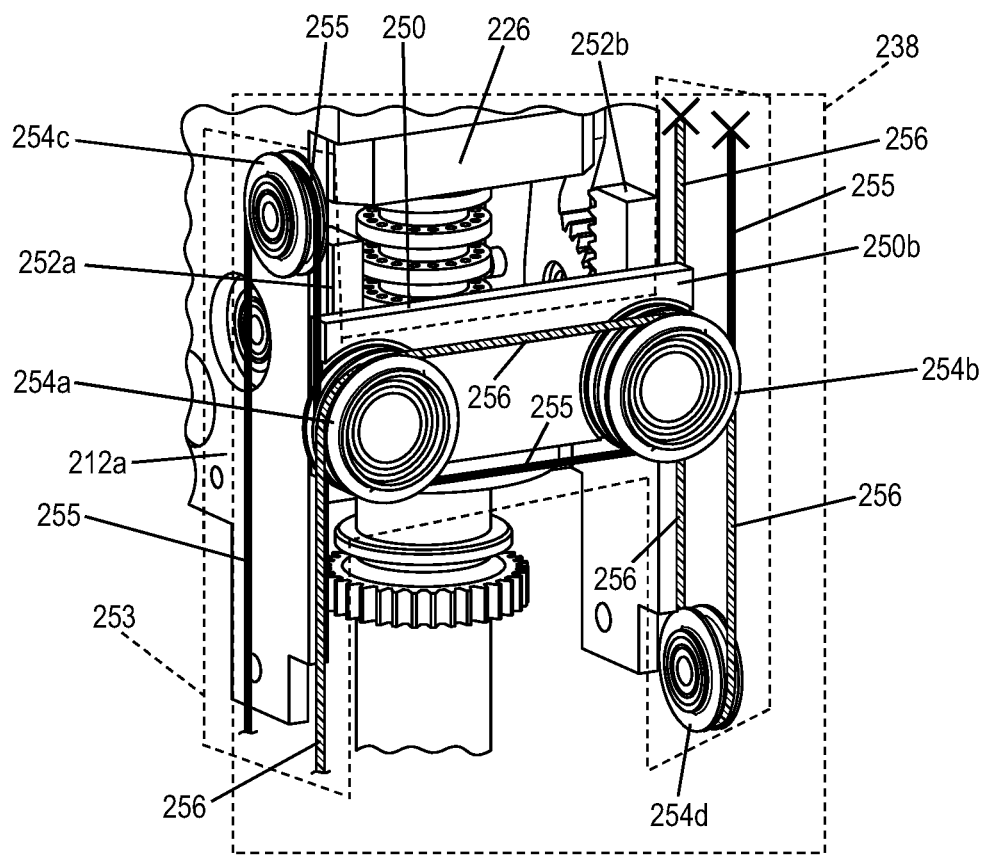
FIG. 10A is magnified rear perspective view of a portion of the surgical instrument of FIG. 8 with certain components removed.

As shown in FIGS. 7 and 9, and in further detail in FIG. 10A, the articulation actuation system 238 includes first and second linkages 240, 242, each extending from a first end 240a, 242a to a second end 240b, 240b. The first end 240a, 242a of first and second linkages 240, 242 each has a fork-like configuration. That is, the first end 240a of the first linkage 240 is in the form of two first prongs 244a, 244b with a first channel 244c extending therebetween, and the first end 242a of the second linkage 242 is in the form of two second prongs 246a, 246b with a second channel 246c extending therebetween. The first channel 244c of the first linkage 240 is configured to receive the first side post 227a of the articulation coupler 226, and the second channel 246c of the second linkage 242 is configured to receive the second side post 227b of the articulation coupler 226. As such, when the tool shaft assembly is coupled to the stage 204, the first and second linkages 240, 242 are on opposite sides of the articulation coupler 226. Further, the second end 240b of the first linkage 240 is in the form of a first pinion gear 248a and the second end 242b of the second linkage 242 is in the form a second pinion gear 248b.

The articulation actuation system 238 further includes an articulation sled 250 and first and second articulation gear racks 252a, 252b that in combination are configured to axially translate relative to the shuttle 212. The first and second articulations gear racks 252a, 252b are spaced apart from each other and are mounted to the front surface 250a of the articulation sled 250. The first articulation gear rack 252a and the second articulation gear rack 252b are configured to engage the first pinion gear 248a of the first linkage 240 and the second pinion gear 248b of the second linkage 242, respectively. In use, the first and second articulation gear racks 252a, 252b translate thereby causing the first and second pinion gears 248a, 248b to rotate. As a result, the rotation of the first and second pinion gears 248a, 248b causes the articulation coupler 226, and thus the master continuum joint 232, to articulate.

Figure 8:
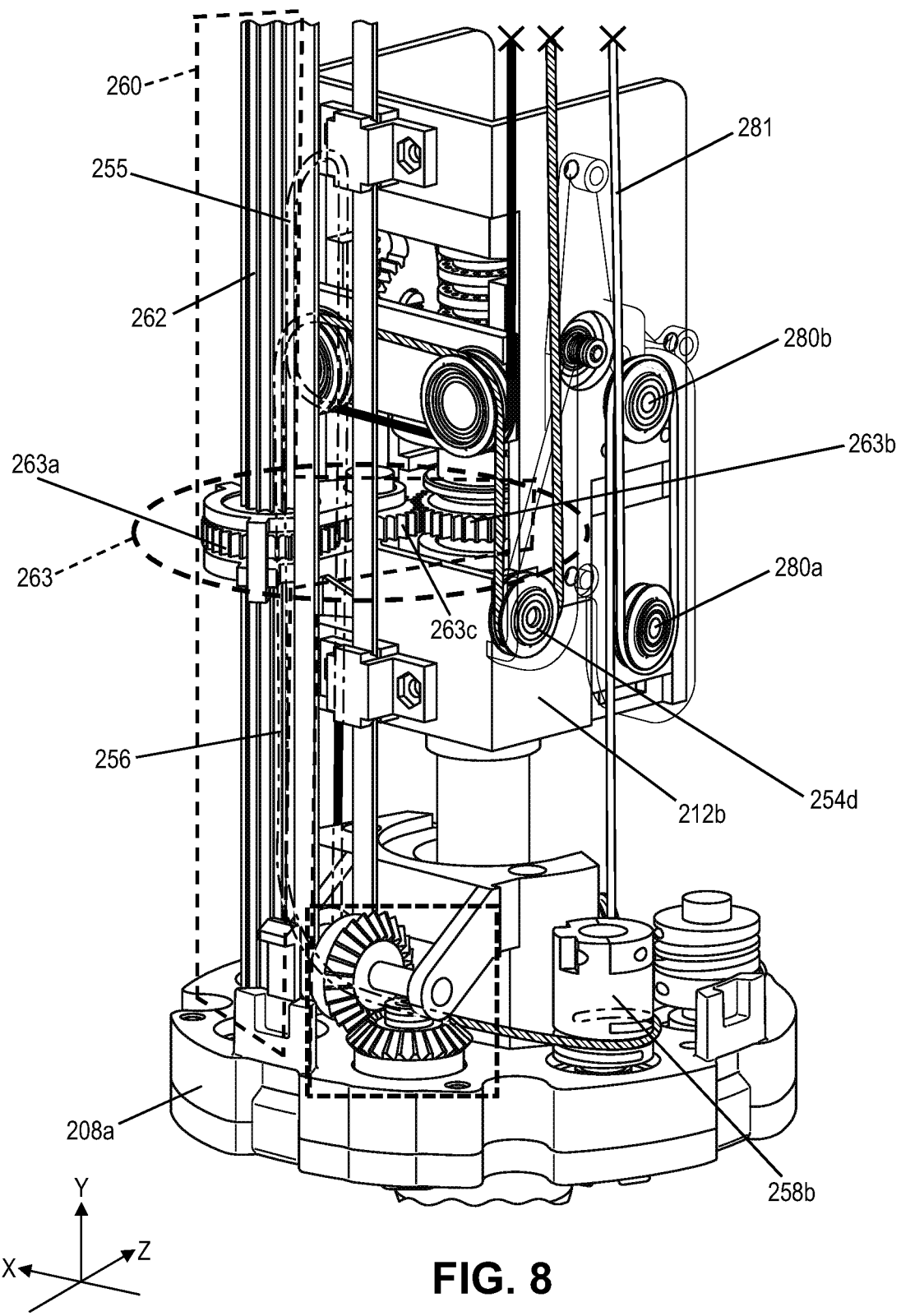
FIG. 8 is a rear perspective view of the portion of the surgical instrument of FIG. 7.
Figure 10B:
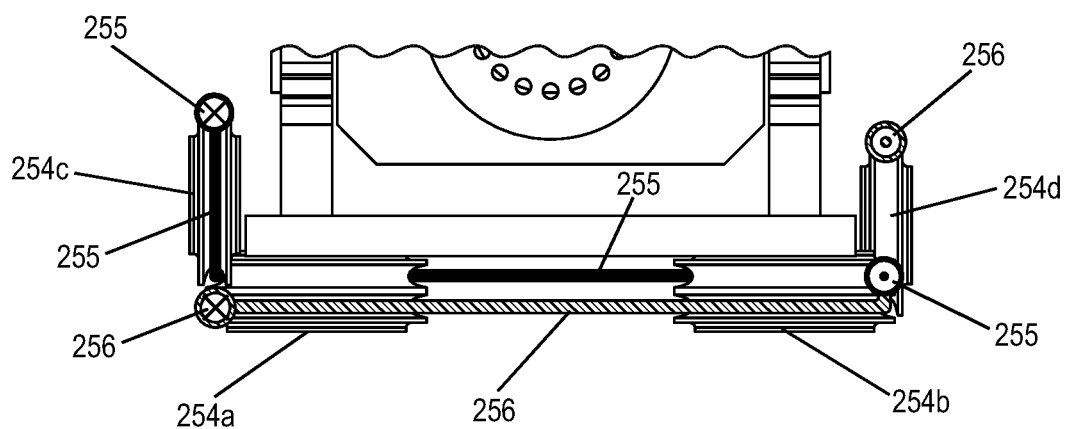
FIG. 10B is a top down view of a portion of the surgical instrument of FIG. 10A with certain components removed.

The articulation actuation system 238 also includes a second pulley assembly 253 that is configured to translate the articulation sled 250, and consequently, the first and second articulation gear racks 252a, 252b. The second pulley assembly 253, which is shown in more detail in FIGS. 10A-10B, includes four idler pulleys 254a, 254b, 254c, 254d and first and second cables 255, 256. In this illustrated embodiment, the four idler pulleys 254a, 254b, 254c, 254d provide a 2×2 pulley path for the first and second cables 255, 256 to thereby allow for antagonistic control of the articulation of the master continuum joint 232. As shown in FIGS. 8 and 10A-10B, the first and second idler pulleys 254a, 254b are each mounted to the back surface 250b of the articulation sled 250 and each include two cable paths, one for the first cable 255 and one for the second cable 256. As shown in FIGS. 10A-10B, the third idler pulley 254c has one cable path for the first cable 255 and is mounted to a first side 212a of the shuttle 212, and the fourth idler pulley 254d has one cable path for the second cable 256 and is mounted to a second, opposing side 212b (see FIG. 8) of the shuttle 212.

While not shown, one end of each of the first and second cables 255, 256 is mounted to the top end 210a of the carriage 210. As illustrated in FIGS. 7 and 8, and in FIG. 12, the opposing end of the first cable 255 is coupled to and the first cable 255 is partially wound about a first motor input capstan 258a and the opposing end of the second cable 256 is coupled to and the second cable 256 is partially wound about a second motor input capstan 258b. The first motor input capstan 258a and second motor input capstan 258b are each mounted and extend through the base plate 208a of the base 206. The first motor input capstan 258a is operably coupled to and therefore actuated by the sixth motor 122 in the motor housing 104. Similarly, the second motor input capstan 258b is operably coupled and actuated by the third motor 116 in the motor housing 104. In use, actuation of the respective motor causes the respective motor input capstan to rotate and either reel (e.g., wind or pull) or feed (e.g., unwind or release) the respective cable through the pulleys to thereby translate the articulation sled 250 in either a first direction (e.g., a direction toward the top end 210a of the carriage 210) or a second direction (e.g., a direction toward the base 206).

For example, the articulation sled 250 can move in the first direction as the first cable 255 is being wound about the first motor input capstan 258a (e.g., in response to first motor input capstan 258a rotating in a first direction (e.g., CCW direction)) and as the second cable 256 is being unwound from the second motor input capstan 258b (e.g., in response to second motor input capstan 258b rotating in the same first direction (e.g., CCW direction). Similarly, the articulation sled 250 can move in the second direction as the first cable 255 is being unwound from the first motor input capstan 258a (e.g., in response to first motor input capstan 258a rotating in a second direction (e.g., CW direction)) and as the second cable 256 is being wound about from the second motor input capstan 258b (e.g., in response to second motor input capstan 258b rotating in the same second direction (e.g., CW direction).

Figure 11A:
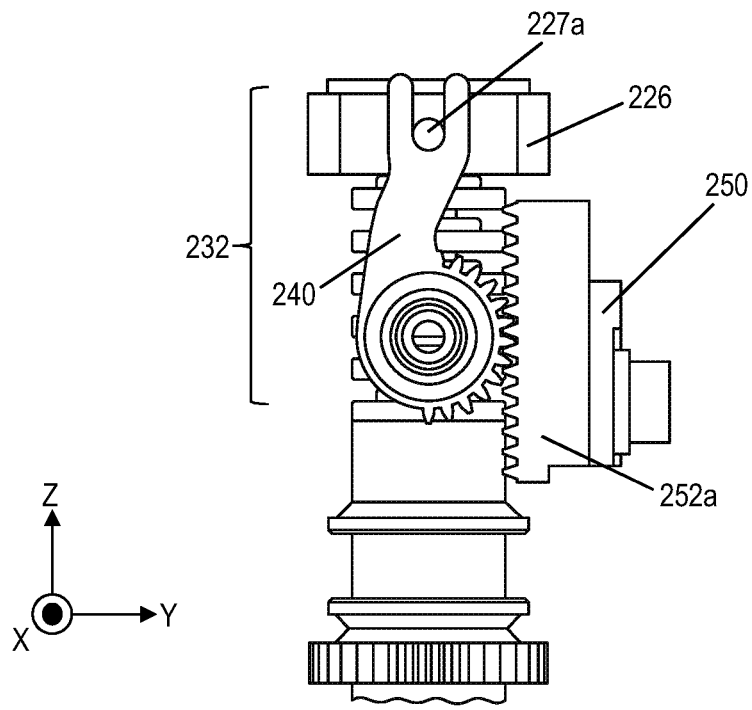
FIG. 11A is a side view of a portion of the tool shaft assembly and a portion of an articulation actuation system of the surgical instrument of FIG. 1, showing the articulation actuation system in an initial portion.
Figure 11B:
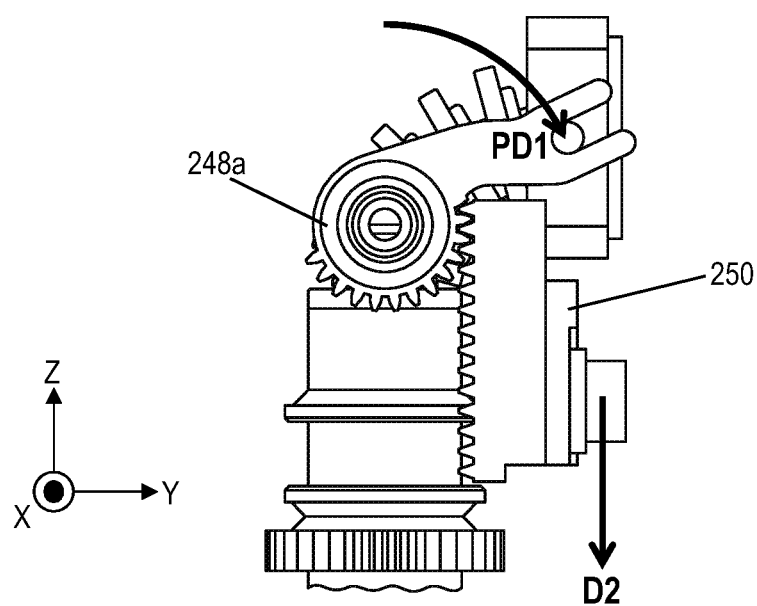
FIG. 11B is a side view of the tool shaft assembly and the articulation actuation system of FIG. 11A, showing the articulation actuation system in a first position.

FIGS. 11A and 11B illustrate axial translation of the articulation sled 250 in the second direction from an initial position (FIG. 11A) to a first position (FIG. 11B). This causes the first and second pinion gears 248a, 248b to rotate in a first rotation direction (e.g., CW direction), and consequently, the articulation coupler 226. Since the articulation coupler 226 is coupled to the master continuum joint 232, this rotation of the articulation coupler 226 causes the master continuum joint to articulate in a first pitch direction PD1 (e.g., CW direction) relative to the longitudinal axis LB of the central body 230 (see FIG. 6). The reverse translation of the articulation sled 250 can return the articulation sled 250 to the initial position (FIG. 11A). Similarly, while not shown, a person skilled in the art will appreciate that translation of the articulation sled 250 from its initial position in the first direction will cause the first and second pinion gears 248a, 248b, and ultimately, the master continuum joint 232 to rotate in a second pitch direction (e.g., CCW direction). As a result, the master continuum joint 232 can articulate ±90 degrees about the longitudinal axis LB of the central body 230 of the tool shaft 222.

The surgical instrument 200 also includes a shaft roll actuation system 260 that is configured to rotate the tool shaft 222 of the tool shaft assembly 202 relative to the motor housing 104 and the electromechanical arm 102 of the robotic surgical system 100. Further, as discussed above, due to the bearing 225, the tool shaft 222 can also rotate relative to the articulation coupler 226 by way of the shaft roll actuation system 260. Since the end effector 228 is coupled to the tool shaft 222, the rotation of the tool shaft 222 therefore effects rotation of the end effector 228. In this illustrated embodiment, the instrument roll actuation system of the robotic surgical system 100 in combination with the shuttle translation actuation system 214, the articulation actuation system 238, and the shaft roll actuation system 260 allows for a full range of motion (e.g., six degrees of freedom) of the end effector 228.

As shown in FIG. 8, the shaft roll actuation system 260 includes a spline shaft 262 that is coupled to and configured to rotate relative to the base plate 208a of the base 206. The spline shaft 262 is operably coupled to the fifth motor 120 in the motor housing 104, and therefore, actuation of the fifth motor 120 causes the spline shaft 262 to rotate (e.g., in CCW direction). The shaft roll actuation system 260 also includes a gear assembly 263 having a spline gear 263a that is coupled to and positioned about the spline shaft 262, a shaft gear 263b that is coupled to and positioned about the tool shaft 222, and an idler gear 263c that is positioned between and engages both the spline gear 263a and the shaft gear 263b. The idler gear 263c allows the spline shaft 262 and the tool shaft 222 to rotate in the same direction. For example, in use, actuation of the fifth motor 120 causes the spline shaft 262 and the spline gear 263a to rotate together in a first direction (e.g., a CW direction). This causes the idler gear 263c to rotate in a second, opposing direction (e.g., a CCW direction). This opposite rotation of the idler gear 263c causes the shaft gear 263b and the tool shaft 222 to rotate in the first direction. A person skilled in the art will appreciate that the rotational direction of the spline and spline gear is dependent at least upon the rotational output of the fifth motor, and therefore, in other embodiments, actuation of the fifth motor can result in counter rotational movement of the components of the gear assembly (e.g., the spline shaft, the spline gear, the tool shaft, and the shaft gear can rotate in the second direction while the idler gear rotates in the first direction). It is also contemplated herein that in other embodiments, the idler gear can be omitted.

Depending on the structural configuration of the end effector, the surgical instrument can include addition actuation systems. For example, in this illustrated embodiment, the surgical instrument also includes a jaw actuation system 264 that is configured to open and close the jaws 228a, 228b of the end effector 228. As shown in FIG. 9, and in more detail in FIG. 13, the jaw actuation system 264 includes first and second jaw coupling rings 266a, 266b that are coupled to and positioned about the tool shaft 222. The first jaw coupling ring 266a has a first T-beam rod 268a coupled thereto, and the second jaw coupling ring 266b has a second T-beam rod 268b coupled thereto. The first and the second T-beam rods 268a, 268b each extend distally through the tool shaft 222 and are operably coupled to a drive rod 270. The drive rod 270 is configured to act on the jaws 228a, 228b to open and close the jaws 228a, 228b. In this illustrated embodiment, the jaws 228a, 228b are biased to an open position.

Figure 13:
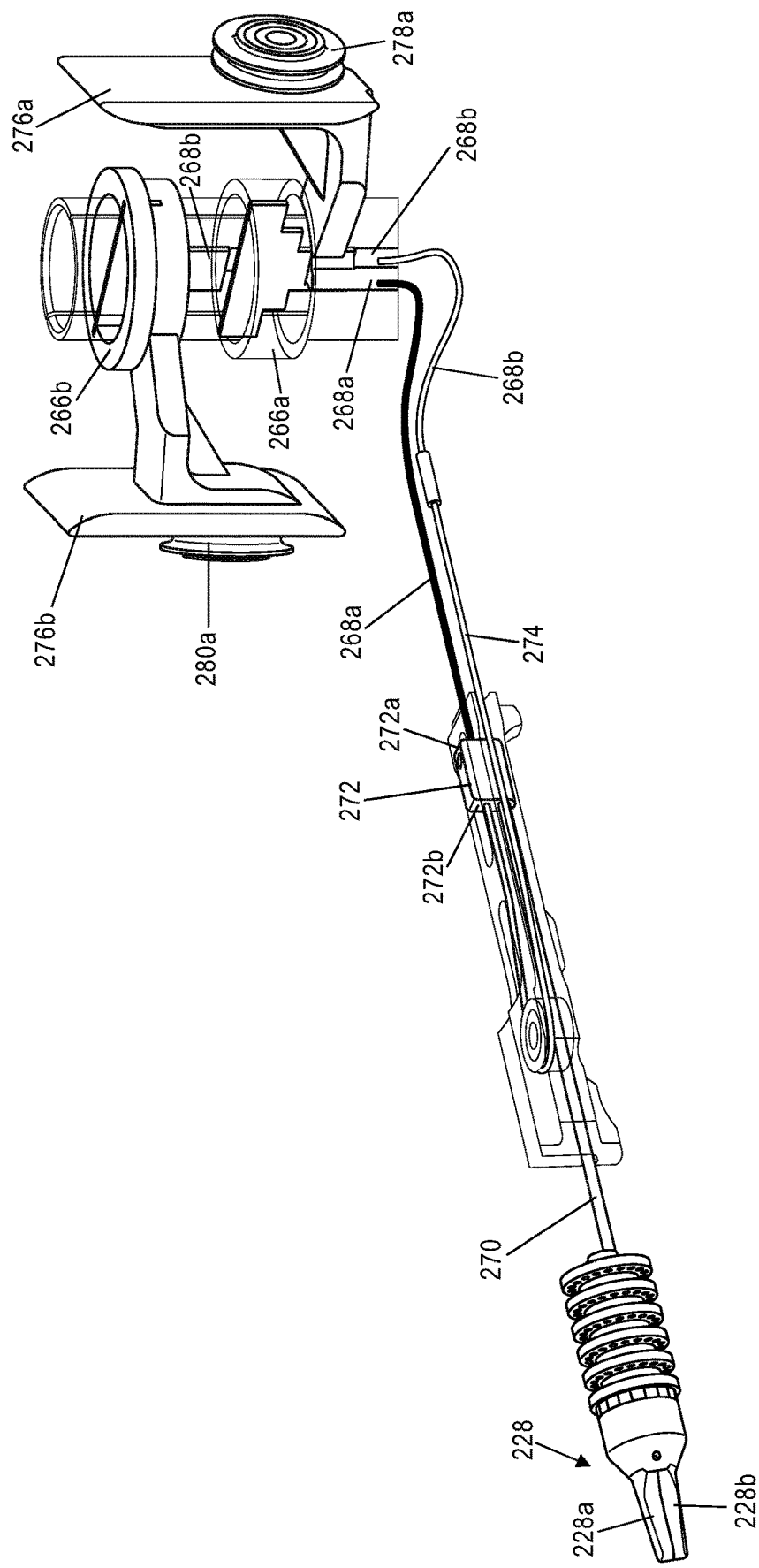
FIG. 13 is a schematic illustration of a portion of a jaw actuation system of the surgical instrument of FIG. 1, showing the mechanical and operational relationship between the jaw actuation system and the end effector.

As schematically illustrated in FIG. 13, the drive rod 270 is coupled to a block 272. The first T-beam rod 268a is coupled to the proximal end 272a of the block 272 and the second T-beam rod 268b is coupled to a cable 274 that is attached to a distal end 272b of the block 272. As a result, translation of the first and second T-beam rods 268a, 268b causes translation of the drive rod 270, and consequently, movement of the jaws 228a, 228b. Since the jaws 228a, 228b are biased to the closed position, when the first and second jaw coupling rings 266a, 266b are pushed toward each other, the drive rod 270 acts on the jaws 228a, 228b to thereby cause the jaws 228a, 228b to open. For example, while not illustrated, in some embodiments, each jaw 228a, 228b include a cam slot, and the cam slots are coupled together via a cam pin. The drive rod 270 can be operably coupled to the cam pin and therefore, when the drive rod 270 is actuated, the drive rod 270 can push, or alternatively pull, the cam pin through the slots in the jaws 228a, 228b. This movement of the cam pin causes the jaws 228a, 228b to pivot away from each other, and thus move from the closed position toward the open position. To move the jaws 228a, 228b from the open position back towards the closed position, the first and second jaw coupling rings 266a, 266b are pushed away from each other to cause the drive rod 270 to reversibly translate. The reversible translation of the drive rod 270 causes the jaws 228a, 228b to move toward each other and thus move from the open position back towards the closed position. In other embodiments, other suitable closing or opening mechanisms can be employed with the jaw actuation system 264 to effect jaw opening and closing of the end effector 228.

As shown in FIGS. 7, 9, and 13 the jaw actuation system 264 also includes first and second jaw actuation forks 276a, 276b that are engaged to the first and second jaw coupling rings 266a, 266b, respectively, and third and fourth pulley assemblies 278, 280 (FIG. 7) that are operably coupled to the first and second jaw actuation forks 276a, 276b, respectively. The translation of the first and second jaw coupling rings 266a, 266b toward and away from each other is effected by the third and fourth pulley assemblies 278, 280 acting on the first and second jaw actuation forks 276a, 276b. The third pulley assembly 278 includes two third pulleys 278a, 278b and a third cable 279, in which one third pulley 278a is directly coupled to the first actuation fork 276a and the other third pulley 278b is coupled to the shuttle 212. The fourth pulley assembly 280 includes two fourth pulleys 280a, 280b and a fourth cable 281, in which one fourth pulley 280a is directly coupled to the second actuation fork 276b and the other fourth pulley 280b is coupled to the shuttle 212.

Figure 12:
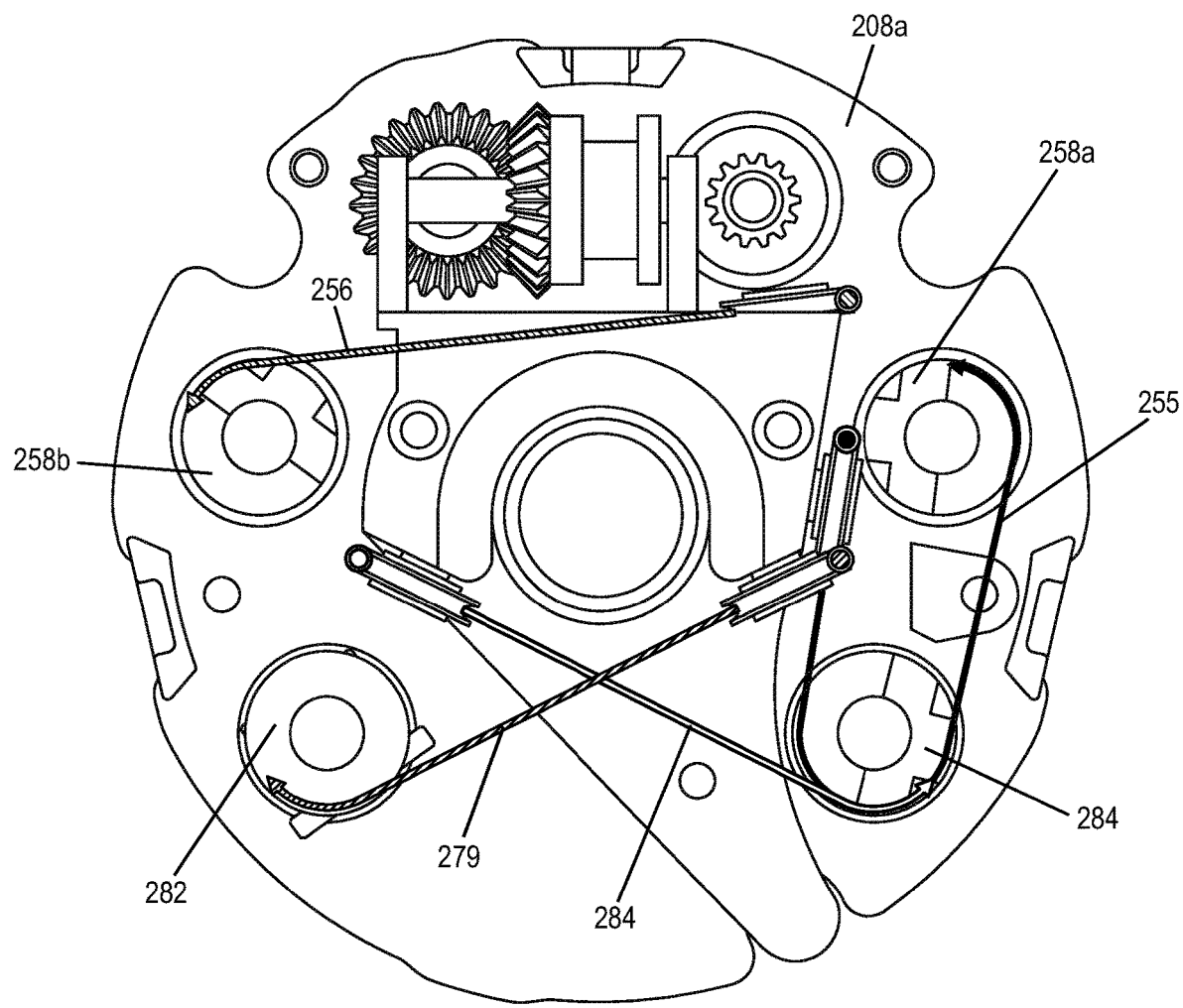
FIG. 12 is a top down view of a portion of the surgical instrument of FIG. 1, showing motor input capstans and cable routing of corresponding pulley systems relative thereto.

While not shown, one end of each of the third and fourth cables 279, 281 is mounted to the top end 210a of the carriage 210. As illustrated in FIGS. 7 and 12, the opposing end of the third cable 279 is coupled to and the third cable 279 is partially wound about a third motor input capstan 282 and the opposing end of the fourth cable 281 is coupled to and the fourth cable 281 is partially would about a fourth motor input capstan 284. The third motor input capstan 282 and fourth motor input capstan 284 are each mounted and extend through the base plate 208a of the base 206. The third motor input capstan 282 is operably coupled to and therefore actuated by the seventh motor 124 in the motor housing 104. Similarly, the fourth motor input capstan 284 is operably coupled and actuated by the second motor 114 in the motor housing 104. In use, actuation of the respective motor causes the respective motor input capstan to rotate and either reel (e.g., wind or pull) or feed (e.g., unwind or release) the respective cable through the pulleys to thereby translate the first and second actuation forks 276a, 276b toward or away from each other to effect jaw movement (e.g., open and closing of the jaws 228a, 228b).

Figure 14:
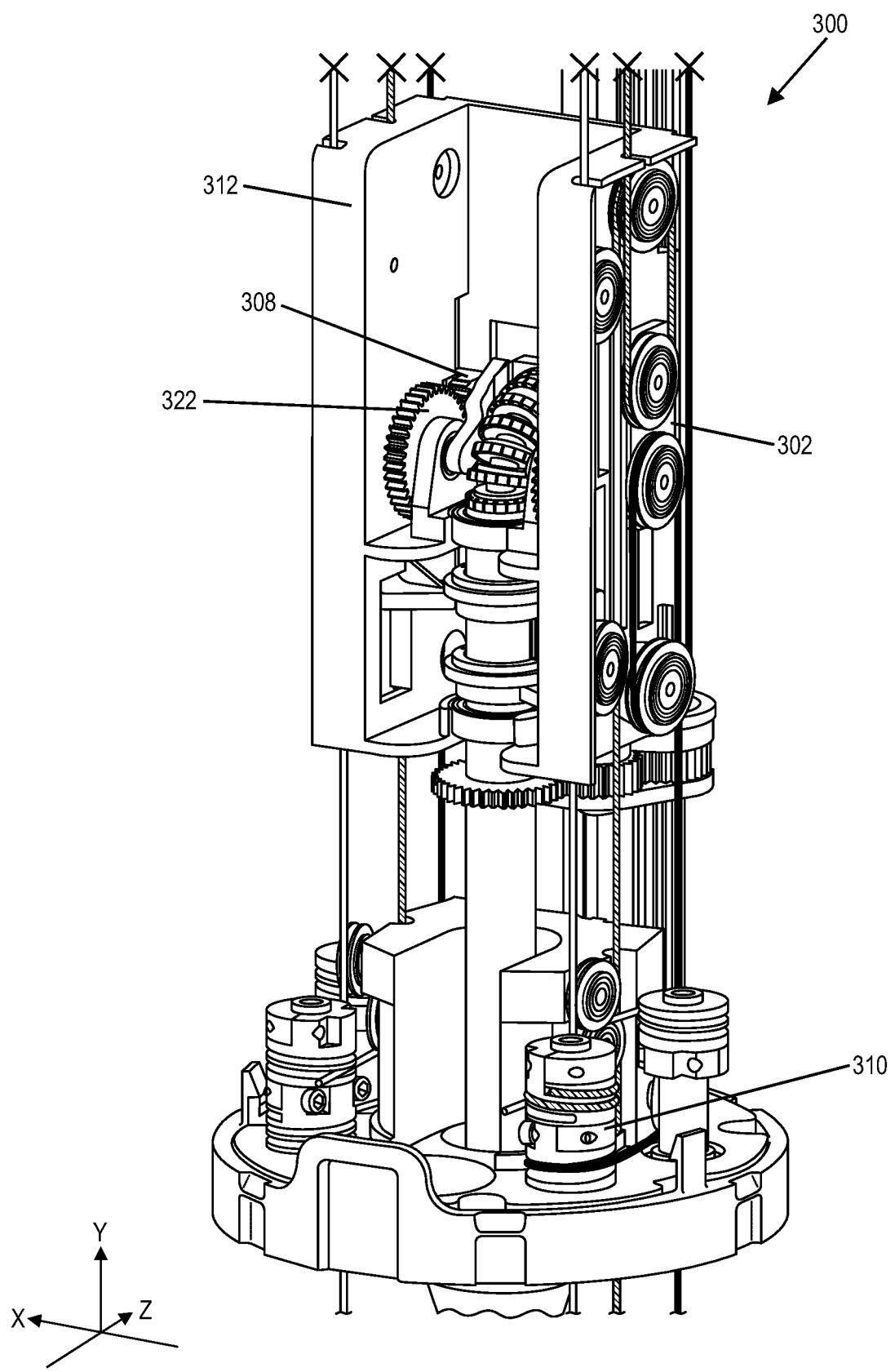
FIG. 14 is a front perspective view of a portion of another embodiment of a surgical instrument.
Figure 15:
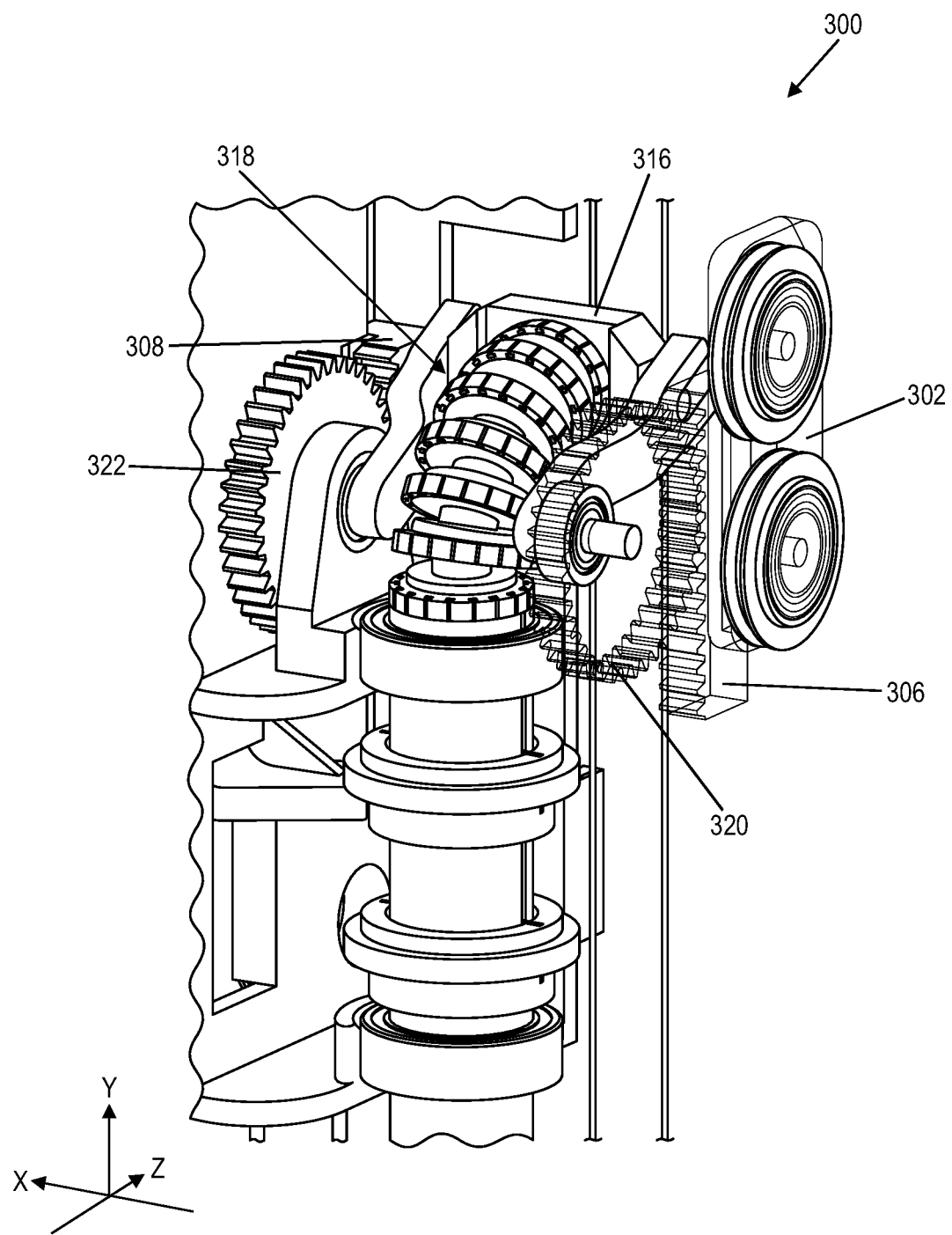
FIG. 15 is a magnified view of a portion of the surgical instrument of FIG. 14 with certain components removed.
Figure 16:
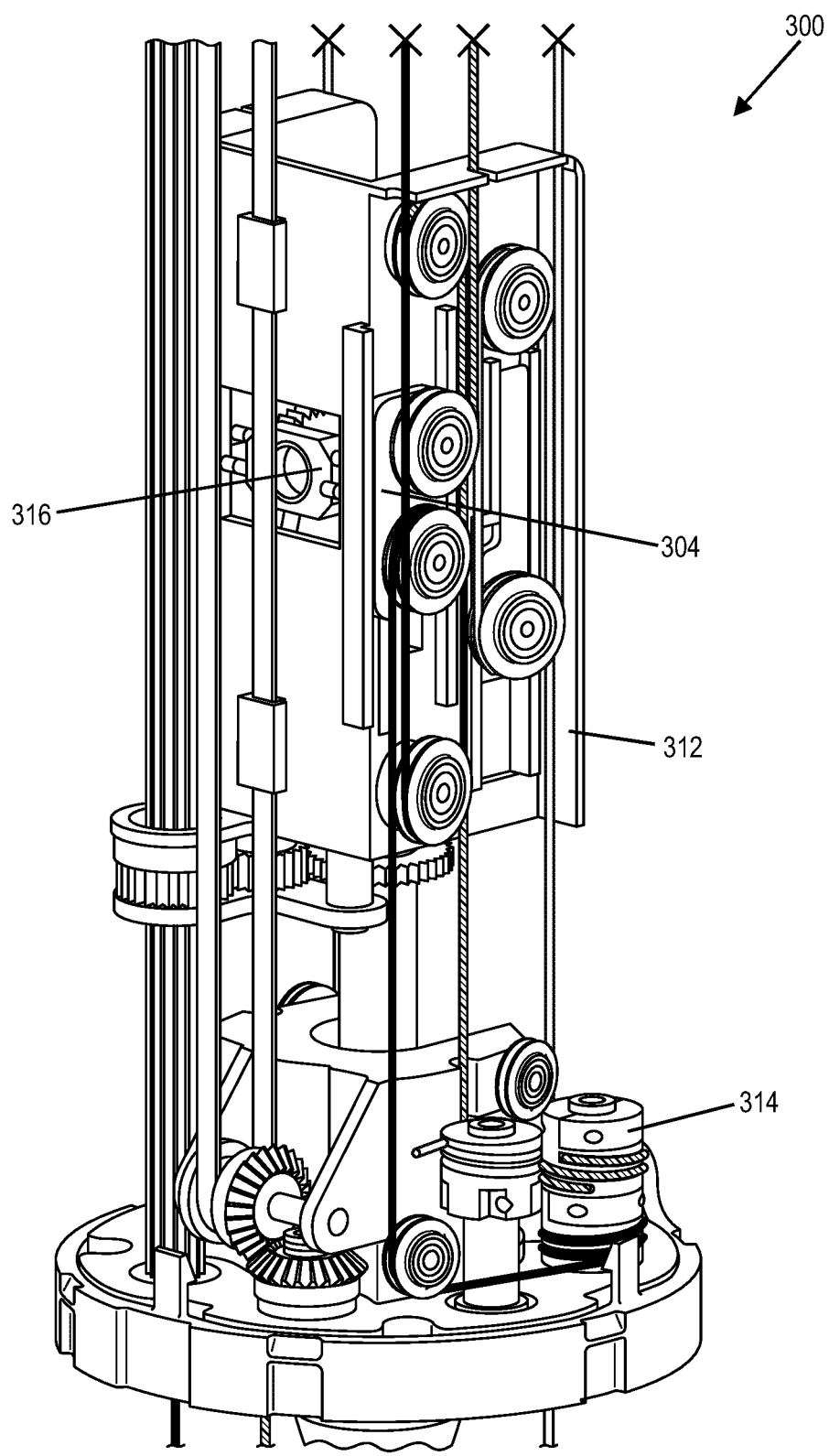
FIG. 16 is a back perspective view of the surgical instrument of FIG. 14.

FIGS. 14-16 illustrate another embodiment of a surgical instrument 300 having two independently actuated articulation sleds 302, 304. For purposes of simplicity, certain components of the surgical instrument 300 are not illustrated. Aside from the differences described in detail below, the surgical instrument 300 can be similar to surgical instrument 200 (FIGS. 1-13) and therefore common features are not described in detail herein.

As shown, the first articulation gear rack 306 is coupled to the first articulation sled 302 and the second articulation gear rack 308 is coupled to the second articulation sled 304. The first articulation sled 302 is operably coupled to a first motor input capstan 310 via a first dual block-and-tackle pulley arrangement. As such, in use, rotation of the first motor input capstan 310 translates the first articulation sled 302 relative to the shuttle 312. Similarly, the second articulation sled 304 is operably coupled to a second motor input capstan 314 via a second dual block-and-tackle pulley arrangement. As such, in use, rotation of the second motor input capstan 314 translates the second articulation sled 304 relative to the shuttle 312. Since translation of the first and second articulation sleds 302, 304 are separately controlled by respective first and second motor input capstans 310, 314, antagonistic control of the rotation of the articulation coupler 316, and consequently the pitch (e.g., movement about the X-axis in the YZ plane) of the master continuum joint 318, can be effected. Further, this separate control can compensate for any backlash that would otherwise occur between the first and second articulation gear racks and the first and second pinion gears 320, 322.

Figure 17:
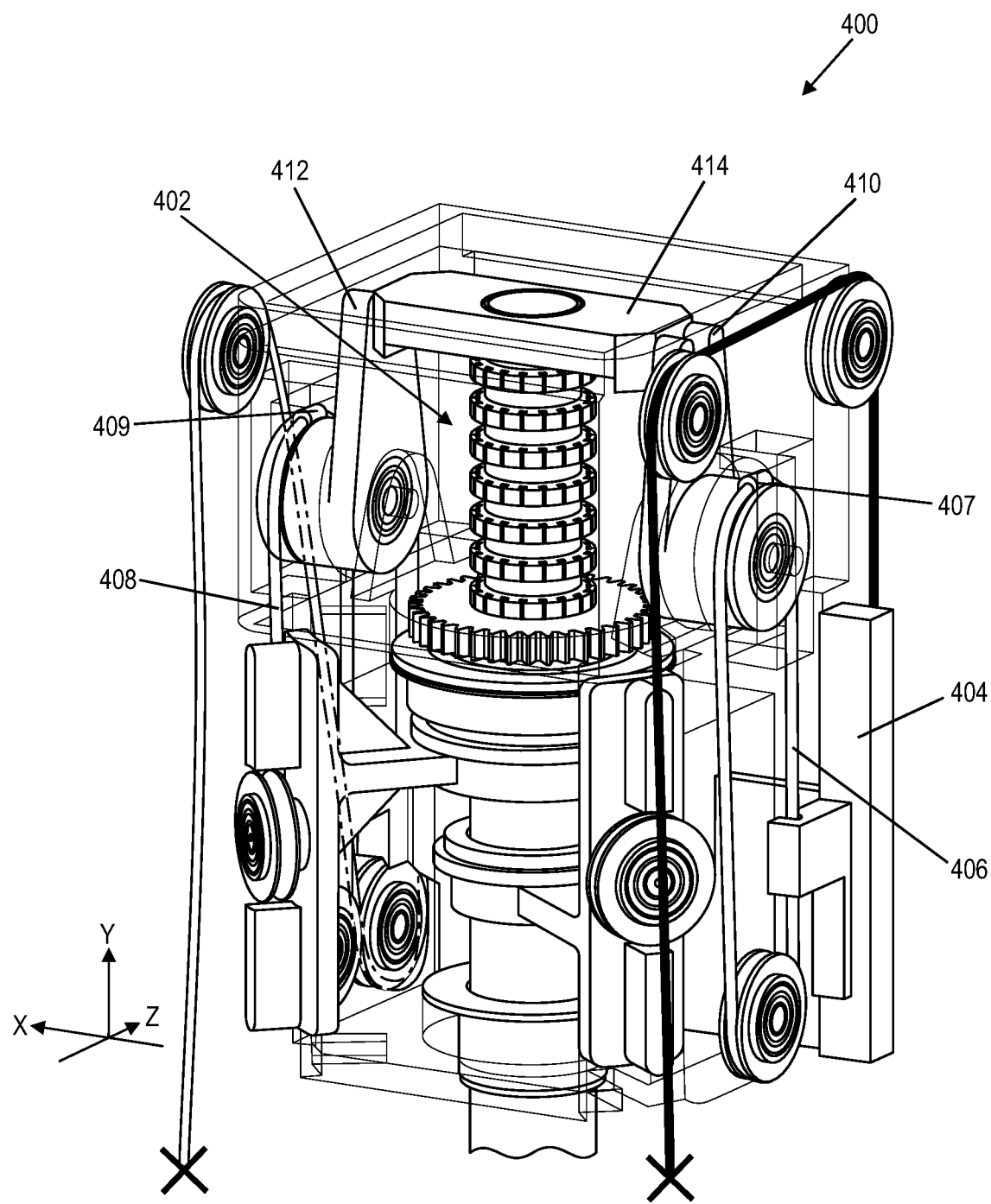
FIG. 17 is a front perspective view of a portion of another embodiment of a surgical instrument.

FIG. 17 illustrates another embodiment of a surgical instrument 400 that is configured to control pitch articulation of the master continuum joint 402 without the use of articulation gear racks and pinion gears. For purposes of simplicity, certain components of the surgical instrument 400 are not illustrated. Aside from the differences described in detail below, the surgical instrument 400 can be similar to surgical instrument 200 (FIGS. 1-13) and therefore common features are not described in detail herein.

As shown, an articulation sled 404 is coupled to a first belt 406 and a second belt 408. The first belt 406 is crimped to the first linkage 410 via a first crimp connector 407, and the second belt 408 is crimped to the second linkage 412 via a second crimp connector 409. As a result, during use, linear movement of the articulation sled 404 causes the first and second belts 406, 408 to move and thereby rotate the first and second linkages 410, 412, respectively. Since the first and second linkages 410, 412 are coupled to opposite sides of the articulation coupler 414, this rotation causes the articulation coupler 414 to rotate, and thus the master continuum joint 402 to pitch (e.g., movement about the X-axis in the YZ plane).

Figure 18:
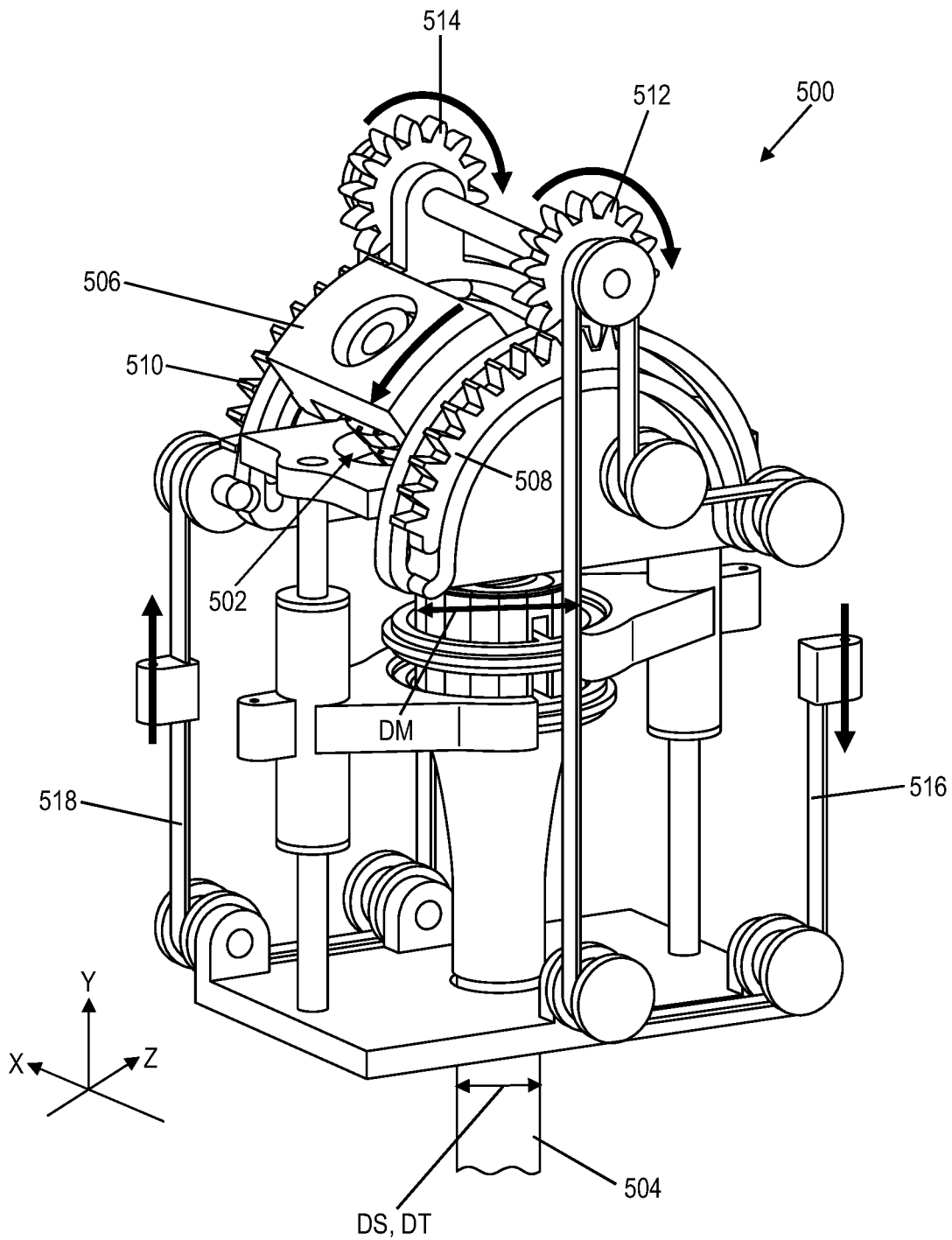
FIG. 18 is a front perspective view of a portion of another embodiment of a surgical instrument.

In some embodiments, a surgical instrument can be designed to control a slave continuum joints with a master continuum joint at a ratio that is not equal (e.g., 2:1 ratio). This can be accomplished, for example, by increasing the diameter of the master continuum joint by the ratio of magnitude. FIG. 18 illustrates an exemplary embodiment of a surgical instrument 500 that is designed to create ±90 degrees of slave articulation (e.g., articulation of the slave continuum joint) with an input of ±45 degrees of master articulation (e.g., articulation of the master continuum joint). For purposes of simplicity, certain components of the surgical instrument 500 are not illustrated. Aside from the differences described in detail below, the surgical instrument 500 can be similar to surgical instrument 200 (FIGS. 1-13) and therefore common features are not described in detail herein. In this illustrated embodiment, the diameter DM of the master continuum joint 502 is twice the diameter DS of the slave continuum joint. While the slave continuum joint is not shown, its diameter DS is equal to the minimum diameter DT of the tool shaft 504.

As further shown, the articulation coupler 506 is coupled to first and second curved articulation gear racks 508, 510, which are positioned on opposite sides of the articulation coupler. Each curved rack 508, 510 is engaged with a respective pinion gear 512, 514, and the pinion gears 512, 514 are antagonistically controlled by respective drive belts 516, 518. In use, movement of the drive belts 516, 518 causes rotation of the pinion gears 512, 514. This results in rotation of the first and second curved articulation gear racks 508, 510, which in turn effects rotation of the articulation coupler 506. In this illustrated embodiment, the pinion gears 512, 514 are grounded and therefore only moves about its respective axis, whereas the first and second curved articulation gear racks and the articulation coupler rotate together about the same axis (e.g., the X-axis). Since the articulation coupler 506 is coupled to the master continuum joint 502, this rotation of the articulation coupler 506 causes the master continuum joint 502 to pitch (e.g., movement about the X-axis in the YZ plane).

Figure 19:
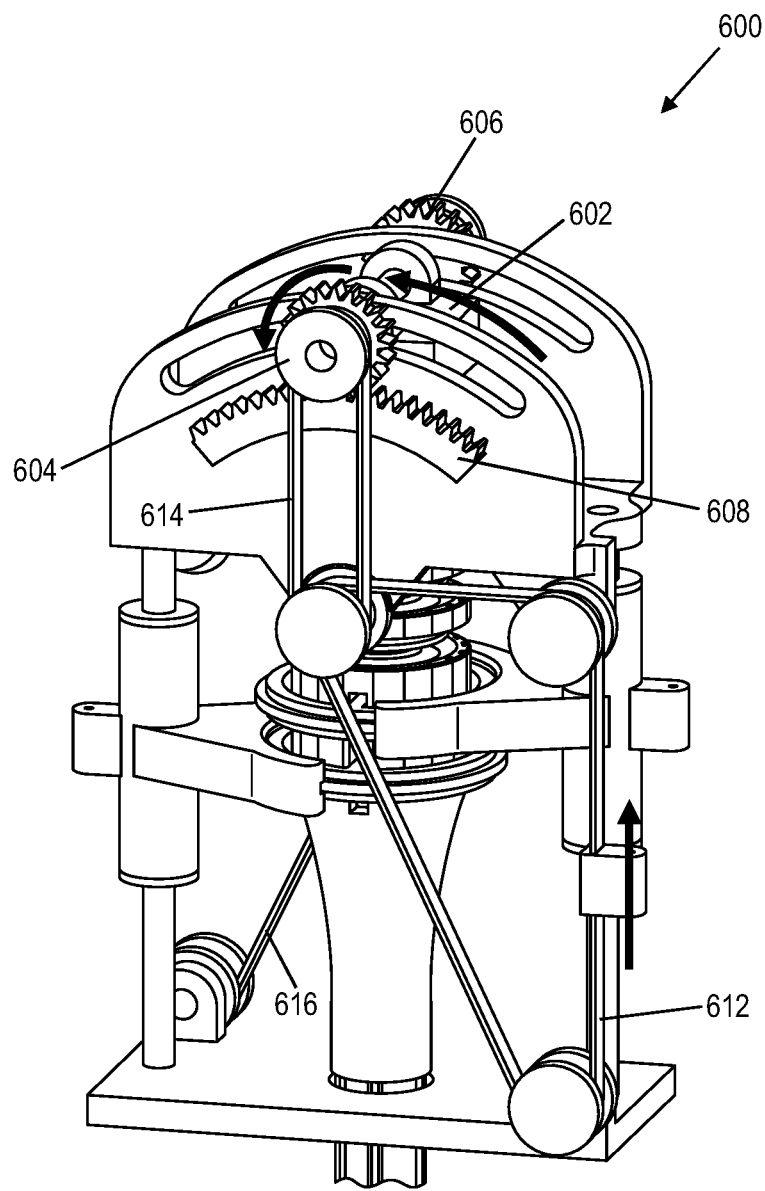
FIG. 19 is a front perspective view of a portion of another embodiment of a surgical instrument.

FIG. 19 illustrates another embodiment of a surgical instrument 600 that is designed to create ±90 degrees of slave articulation (e.g., articulation of the slave continuum joint) with an input of ±45 degrees of master articulation (e.g., articulation of the master continuum joint). For purposes of simplicity, certain components of the surgical instrument 600 are not illustrated. Aside from the differences described in detail below, the surgical instrument 600 can be similar to surgical instrument 500 (FIG. 18) and therefore common features are not described in detail herein.

As shown, the articulation coupler 602 is coupled to first and second pinion gears 604, 606 that are positioned on opposite sides of the articulation coupler 602. The first pinion gear 604 is engaged with a first curved articulation gear rack 608, and the second pinion gear 606 is engaged with a second curved articulation gear rack 610 (obstructed). The first and second pinion gears 604, 606 are actuated and antagonistically controlled by four drive belts 612, 614, 616, 618 (obstructed). In this illustrated embodiment, during use, the first and second pinion gears 604, 606 move with the articulation coupler 602, and thus, the first and second pinion gears 604, 606 travel along respective first and second articulation racks 608, 610. That is, the first and second articulation gear racks 608, 610 are grounded, and therefore, they remain stationary relative to the first and second pinion gears 604, 606.

Figure 20:
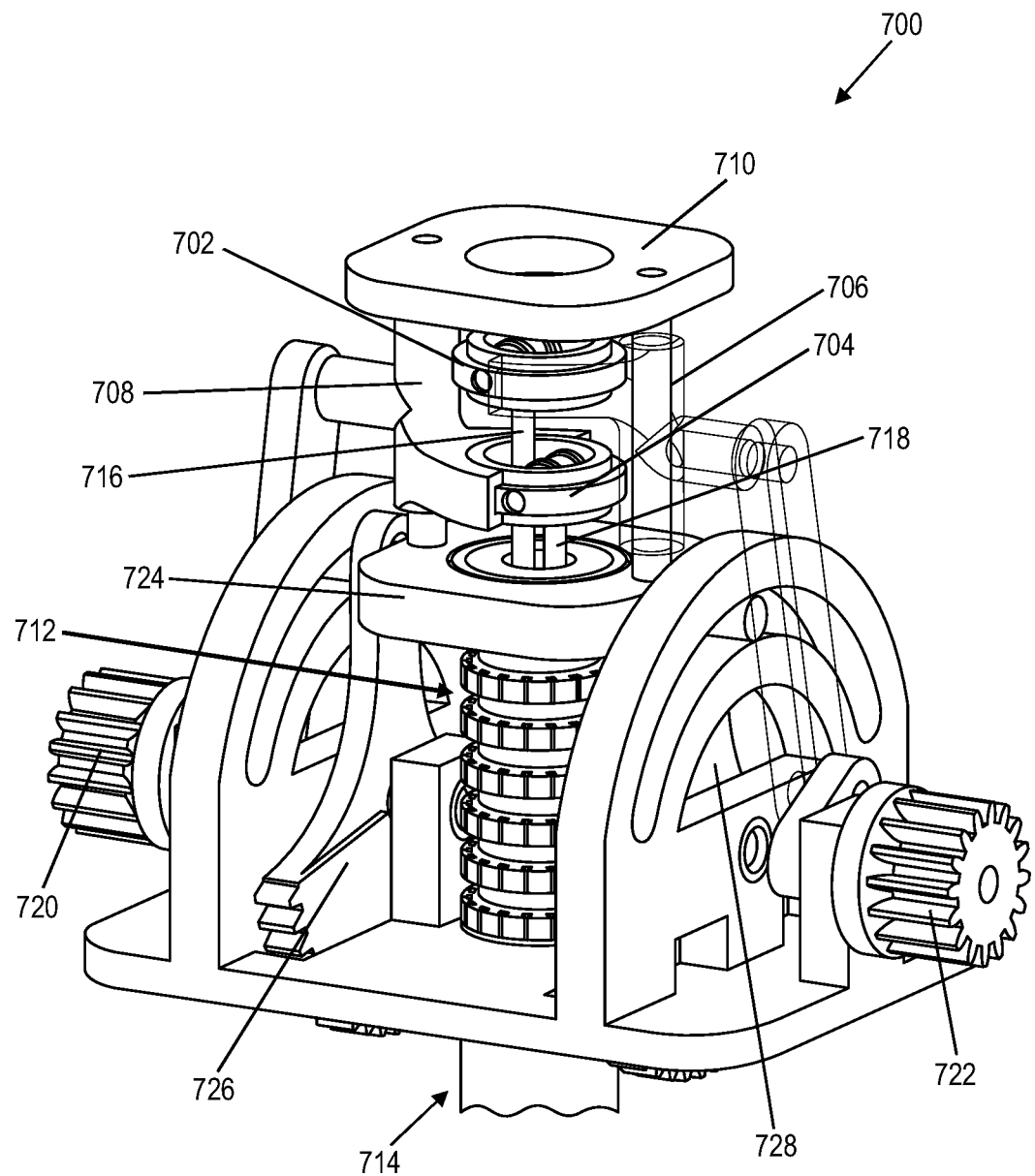
FIG. 20 is a front perspective view of a portion of another embodiment of a surgical instrument, showing the surgical instrument in an unarticulated position.
Figure 21:
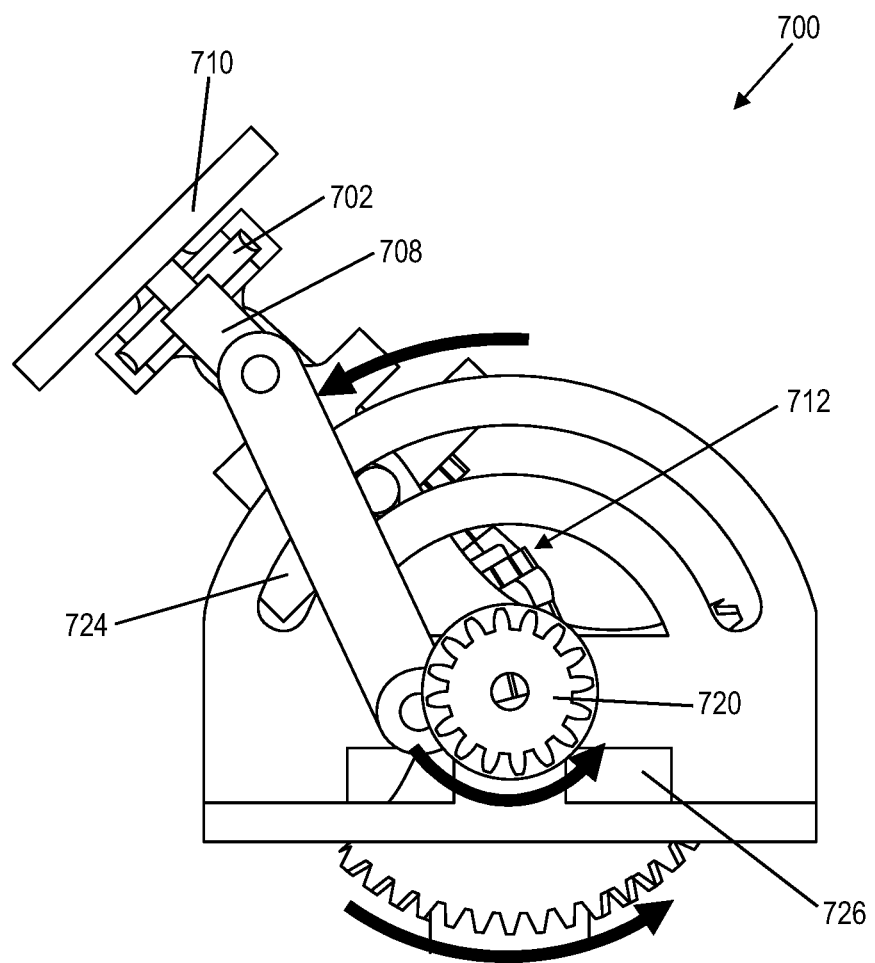
FIG. 21 is a side view of a portion of the surgical instrument of FIG. 20, showing the surgical instrument in a first articulated position.

In some embodiments, a surgical instrument can be designed with a jaw control mechanism that does not bypass the master continuum joint. FIGS. 20 and 21 illustrate an exemplary embodiment of a surgical instrument 700. For purposes of simplicity, certain components of the surgical instrument 700 are not illustrated. Aside from the differences described in detail below, the surgical instrument 700 can be similar to surgical instrument 200 (FIGS. 1-13) and therefore common features are not described in detail herein.

The surgical instrument 700 includes a jaw control mechanism that includes first and second jaw coupling rings 702, 704 that are coupled to respective first and second jaw actuation forks 706, 708. The coupling rings 702, 704 and the jaw actuation forks 706, 708 are positioned between a proximal end cap 710 and a master continuum joint 712 of the tool shaft 714. The first and second jaw coupling rings 702, 704 each have a respective rod 716, 718 that is coupled thereto and extends distally through the tool shaft 714, including the master continuum joint 712. While not shown, the rods 716, 718 are operably coupled to respective jaws of an end effector at the distal end of the tool shaft 714, and the rods 716, 718 are configured to act on the jaws to open and close the jaws.

As further shown in FIG. 20, the first jaw actuation fork 706 is operably coupled to a first jaw control gear 720, and the second jaw actuation fork 708 is operably coupled to a second jaw control gear 722. While not shown, the first and second jaw control gears 720, 722 can be operably coupled to and actuated by respective motor input capstans. During use, when the first and second jaw control gears 720, 722 are actuated, they drive rotation of the first and second actuation forks 706, 708. Depending on the rotational direction, the first and second actuation forks 706, 708 move the first and second jaw coupling rings 702, 704 toward or away from each other, and thus, translate the rods 716, 718 to effect opening and closing of the jaws.

The surgical instrument 700 also includes an articulation coupler 724 that is coupled to and configured to articulate the master continuum joint 712. In this illustrated embodiment, first and second articulation gear arms 726, 728 are coupled to opposing sides of the articulation coupler 724 and are configured to rotate the articulation coupler 724. While not shown, the first and second articulation gear arms 726, 728 can be operably coupled to and actuated by respective motor input capstans, or in some embodiments, to the same motor input capstan. As shown in FIG. 21, when the first and second articulation gear arms 726, 728 rotate (e.g., in response to being actuated via motor input capstan(s), they cause rotation of the articulation coupler 724. The rotation of the articulation coupler 724 effects pitch of the master continuum joint (e.g., movement about the X-axis in the YZ plane). Further, given the proximal position of the jaw control mechanism relative to the master continuum joint 712, there is coordinated motion between the first and second jaw control gears 720, 722 and the first and second articulation gear arms 726, 728. This allows for master and slave joint articulation to occur with or without jaw actuation. For example, as shown in FIG. 21, to prevent jaw actuation during articulation of the master continuum joint 712, and thus the slave continuum joint (not shown), the first and second jaw control gears 720, 722 rotate with the first and second articulation gear arms 726, 728.

Figure 22:
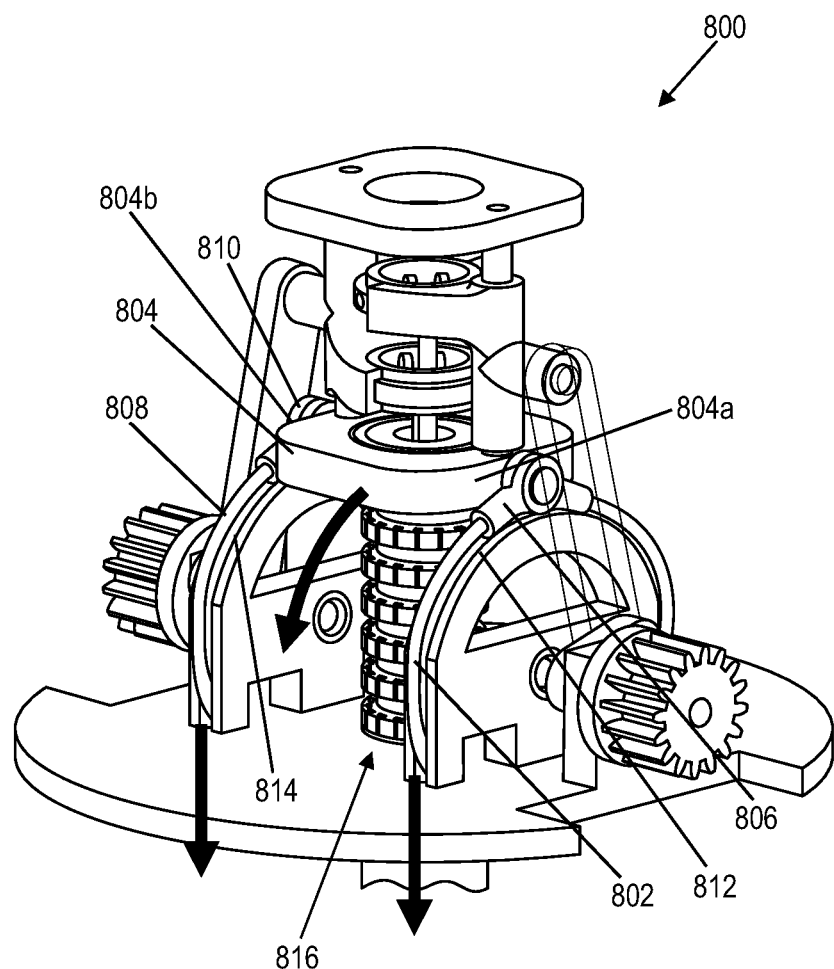
FIG. 22 is a front perspective view of a portion of another embodiment of a surgical instrument.
Figure 23:
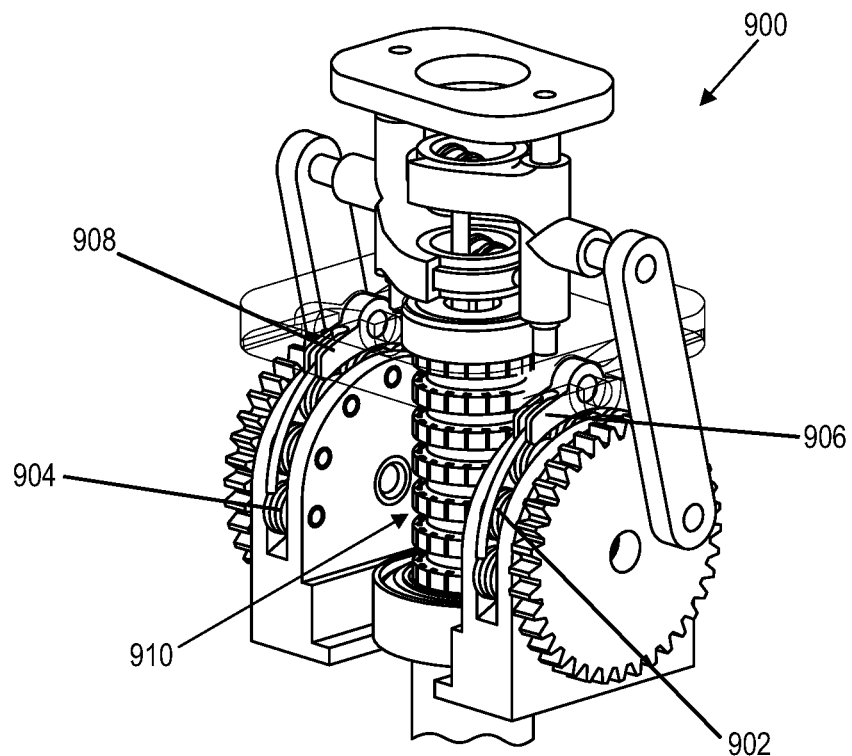
FIG. 23 is a front perspective view of a portion of another embodiment of a surgical instrument, showing the surgical instrument in an unarticulated position.
Figure 24:
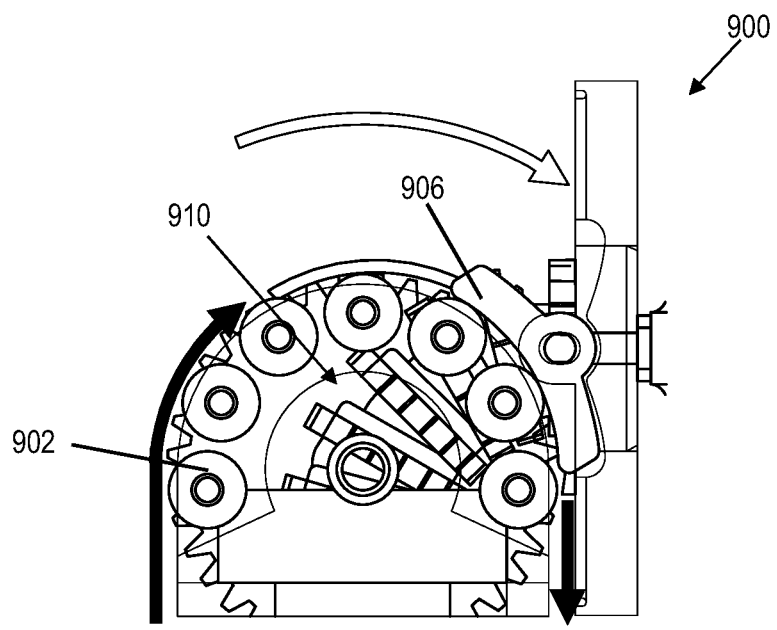
FIG. 24 is a side view of a portion of the surgical instrument of FIG. 23, showing the surgical instrument in a first articulated position.

In some embodiments, tensioned guide cables can be used to control articulation of the master continuum joint. For example, as shown in FIG. 22, a surgical instrument 800 includes a first cable 802 directly coupled to a first side 804a of the articulation coupler 804 via a first coupling element 806 and a second cable 808 directly coupled to a second, opposite side 804b of the articulation coupler 804 via a second coupling element 810. While not shown, the first and second cables 802, 808 can also be directly coupled to and actuated by respective first and second motor input capstans. Upon actuation, the first and second cables 802, 808 move along respective first and second guide tracks 812, 814 and rotate the articulation coupler 804 to thereby articulate the master continuum joint 816. In another embodiment, the guide tracks can be replaced with tracks of guide rollers to minimize friction that would otherwise be created when the guide tracks are traversed by the first and second cables. For example, as shown in FIGS. 23 and 24, the surgical instrument 900 includes first and second tracks of guide rollers 902, 904 and first and second sleds 906, 908. The first and second sleds 906, 908 are configured to transverse the first and second tracks of guide rollers 902, 904, respectively, and transmit the cable motion to the master continuum joint 910 (see FIG. 24).

Figure 25:
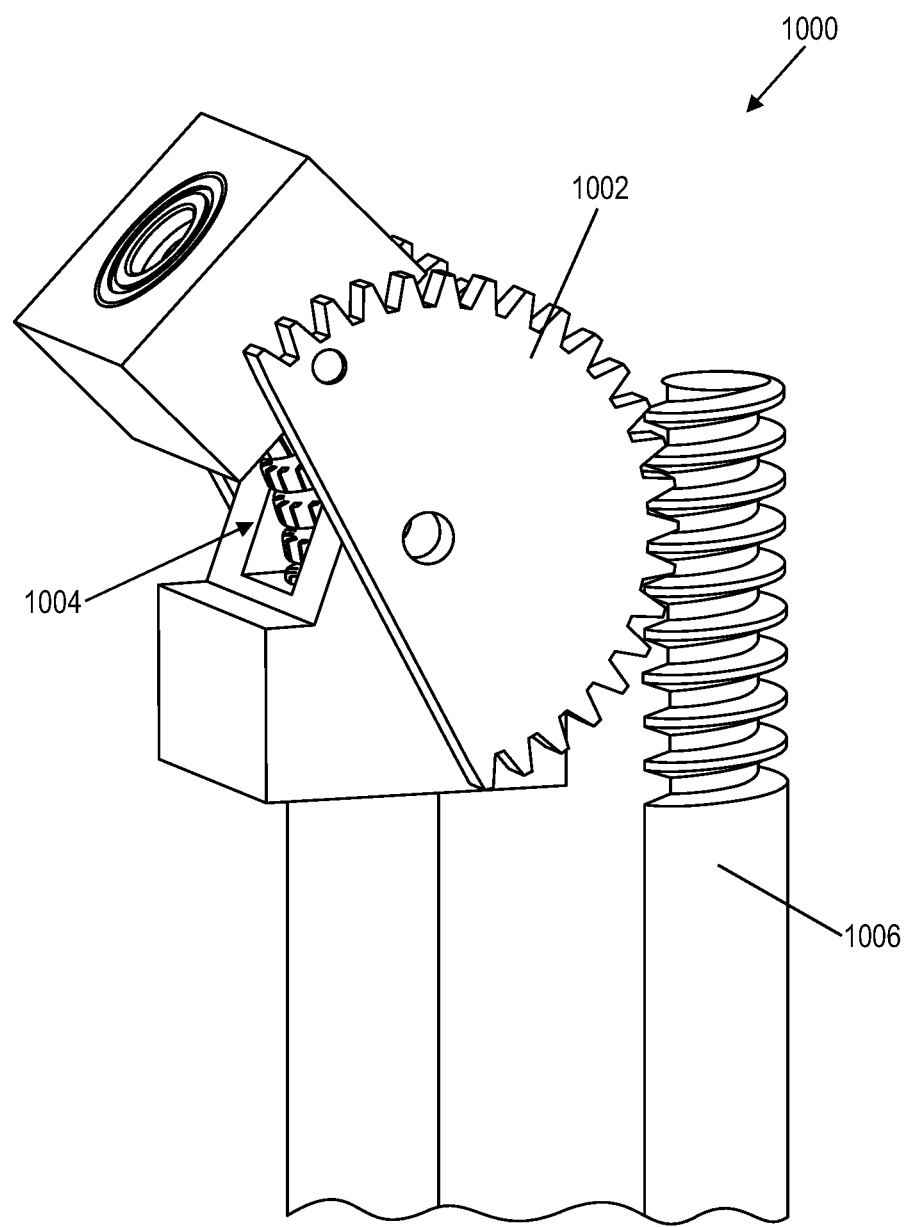
FIG. 25 is a perspective view of a portion of another embodiment of a surgical instrument, showing the surgical instrument in an articulated position.

In some embodiments, a lead screw can be used to control articulation of the master continuum joint. For example, FIG. 25 illustrates an exemplary embodiment of a surgical instrument 1000 that includes a sector gear 1002 that is operably coupled to the master continuum joint 1004, and a lead screw 1006 that is engaged with the sector gear 1002. The lead screw 1006 is operably coupled to a motor (not shown). As a result, when the motor is actuated, the lead screw 1006 is configured to cause rotational movement of the sector gear 1002 to thereby articulate the master continuum joint 1004, as shown in FIG. 25.

Figure 26:
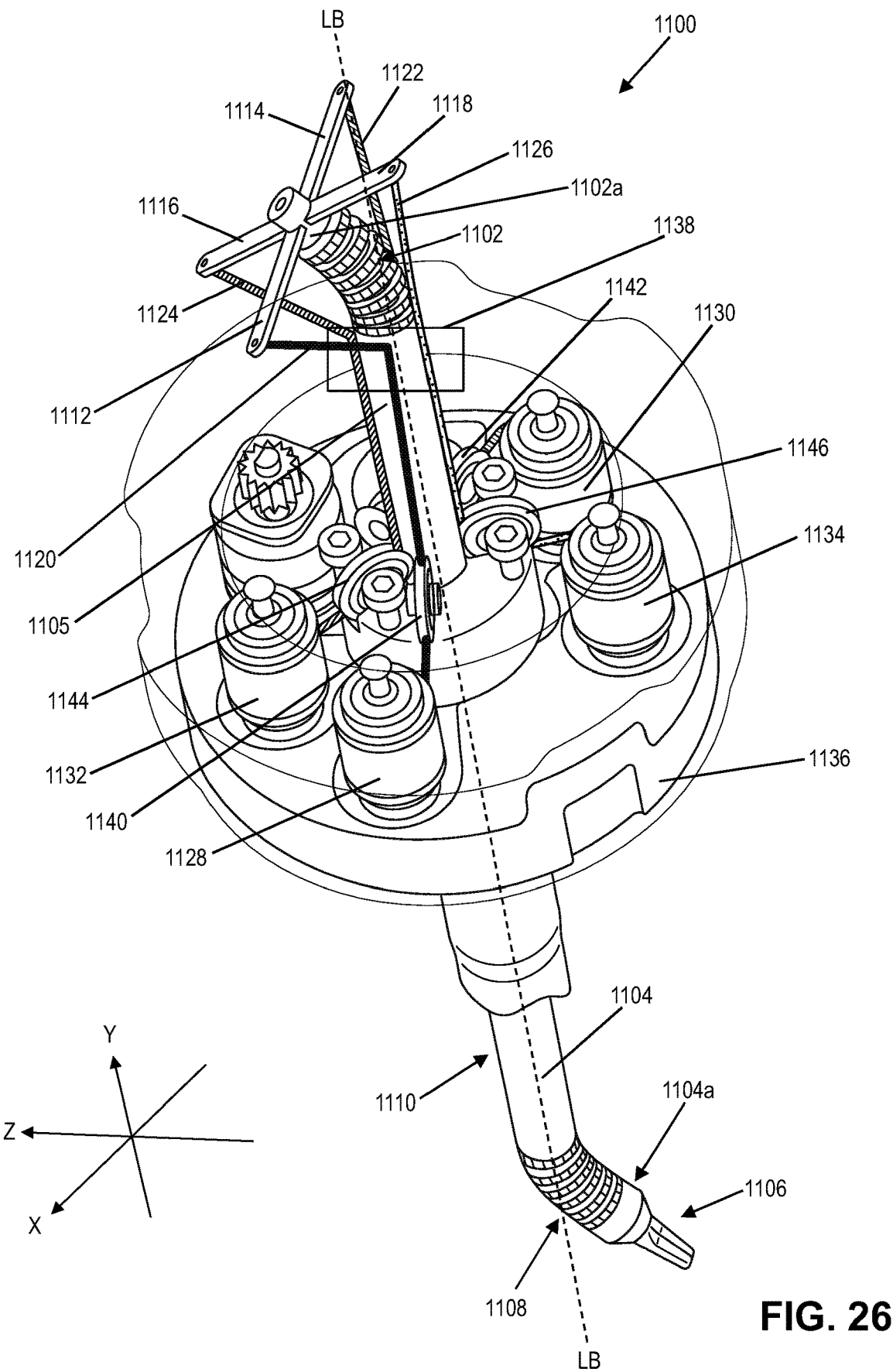
FIG. 26 is a top down perspective view of a portion of another embodiment of a surgical instrument, showing the surgical instrument in an articulated position.

In some embodiments, a surgical instrument can be configured to articulate the master continuum joint within two degrees of freedom (e.g., pitch and yaw). For example, FIG. 26 illustrate an exemplary embodiment of a surgical instrument 1100 that includes an articulation actuation system that is configured to enable a master continuum joint 1102 to both pitch and yaw. For purposes of simplicity, certain components of the surgical instrument 1100 are not illustrated. Aside from the differences described in detail below, the surgical instrument 1100 can be similar to surgical instrument 200 (FIGS. 1-13) and therefore common features are not described in detail herein.

As shown, the surgical instrument 1100 has a tool shaft 1104 having an end effector 1106 coupled to a distal end 1104a thereof. The tool shaft 1104 includes the master continuum joint 1102, a slave continuum joint 1108, and a central body 1110 extending therebetween. The master and slave continuum joints 1102, 1108 are operably coupled to each other such that movement of the master continuum joint 1102 causes parallel movement of the slave continuum joint 1108 while maintaining a position of the longitudinal axis LB of the central body 1110 to thereby effect articulation of the end effector 1106 in two different planes about the central body 1110.

The articulation actuation system is coupled to the master continuum joint 1102 and includes four lever arms 1112, 1114, 1116, 1118 and four cables 1120, 1122, 1124, 1126. The four lever arms 1112, 1114, 1116, 1118 are coupled to and extend outward from the proximal end 1102a of the master continuum joint 1102, in which each lever arm 1112, 1114, 1116, 1118 extends outward in a different direction. More specifically, the first and second lever arms 1112, 1114, extend in opposite directions along the X-axis and the third and fourth lever arms 1116, 1118 extend in opposite directions along the Z-axis. As a result, each lever arm 1112, 1114, 1116, 1118 is configured to move the master continuum joint 1102 in a respective one direction within the XY and YZ planes. As such, the master continuum joint 1102 can articulate within two degrees of freedom, which in this illustrated embodiment, is pitch and yaw.

As shown in FIG. 26, each cable 1120, 1122, 1124, 1126 is coupled to and extends from a respective lever arm 1112, 1114, 1116, 1118 to a respective motor 1128, 1130, 1132, 1134. Each motor 1128, 1130, 1132, 1134 is located within a motor housing 1136 that is coupled to the tool shaft 1104. During use, each motor 1128, 1130, 1132, 1134 is configured to tension the respective cable 1120, 1122, 1124, 1126 and selectively pull the respective cable 1120, 1122, 1124, 1126 to thereby cause movement of the respective lever arm 1112, 1114, 1116, 1118. Further, as shown, each cable 1120, 1122, 1124, 1126 is routed through an upper pulley, which is generally illustrated as box 1138, along a portion of an outer surface 1105 of the tool shaft 1104 and then through a lower pulley 1140, 1142, 1144, 1146. During use, this cable routing helps generate a sufficient amount of mechanical advantage such that movement of any of the four levers 1112, 1114, 1116, 1118 can effectively move the master continuum joint 1102 when one or more of the cables 1120, 1122, 1124, 1126 are being pulled.

Figure 27:
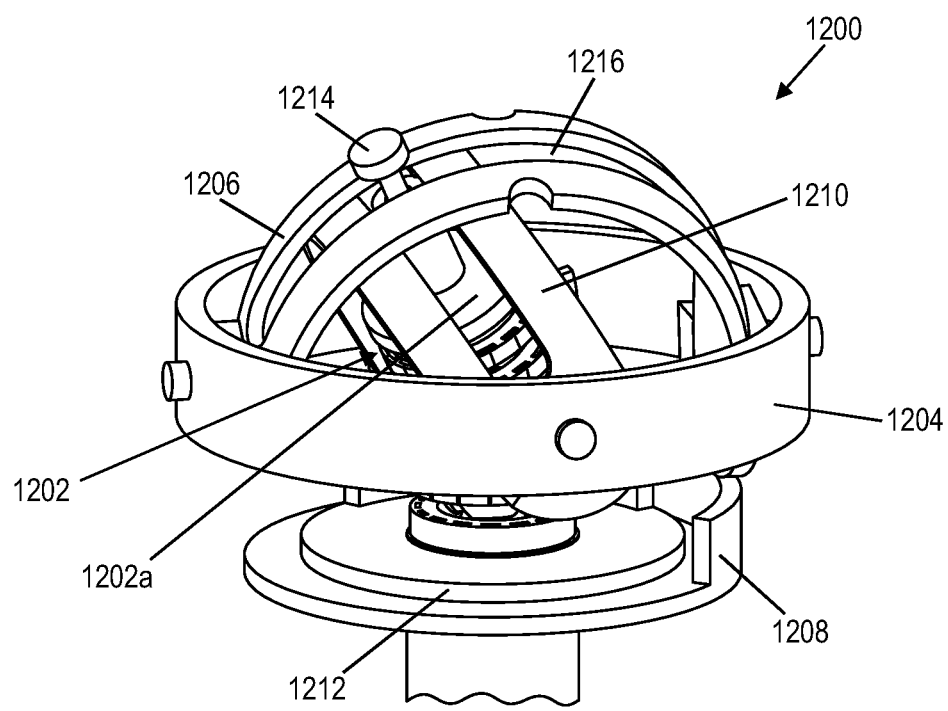
FIG. 27 is a perspective view of a portion of another embodiment of a surgical instrument, showing the surgical instrument in an articulated position.
Figure 28:
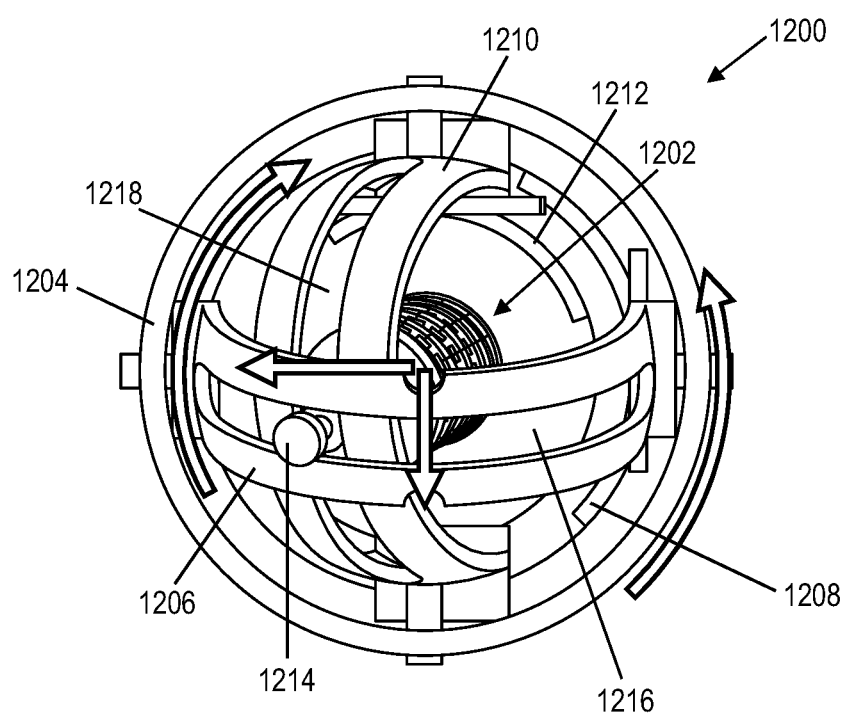
FIG. 28 is a top view of the surgical instrument of FIG. 27.

FIGS. 27 and 28 illustrate another embodiment of a surgical instrument 1200 that includes an articulation actuation system that is configured to enable a master continuum joint 1202 to both pitch and yaw. For purposes of simplicity, certain components of the surgical instrument 1200 are not illustrated. Aside from the differences described in detail below, the surgical instrument 1200 can be similar to surgical instrument 200 (FIGS. 1-13) and therefore common features are not described in detail herein.

As shown, the articulation actuation system has a gyroscope configuration and includes a cart 1204, a pitch control arm 1206 that is pivotally coupled to the cart 1204 and engaged with a pitch control rack 1208, and a yaw control arm 1210 that is pivotally coupled to the cart 1204 and engaged with a yaw control rack 1212. Further, a control input 1214 extends outward from a proximal end 1202a of the master continuum joint 1202 and through first and second curved slots 1216, 1218 that are defined in the pitch and yaw control arms 1206, 1210, respectively. As a result, the master continuum joint 1202 is coupled to and is configured to be manipulated by both the pitch and yaw control arms 1206, 1210, as schematically illustrated in FIG. 28.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein, respectively, with reference to the top end (e.g., the end that is farthest away from the surgical site during use) and the bottom end (e.g., the end that is closest to the surgical site during use) of a surgical instrument, respectively, that is configured to be mounted to a robot. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A robotic surgical system, comprising:
an electromechanical arm;
a motor housing configured to be mounted to the electromechanical arm, the motor housing having at least one motor disposed therein;
a tool shaft extending from the motor housing, the tool shaft including
a central body having a proximal-most end, a distal-most end, and a longitudinal axis extending therebetween, and a joint assembly having a master joint coupled to the proximal-most end of the central body and a slave joint coupled to the distal-most end of the central body;

an end effector coupled to a distal-most end of the slave joint, the end effector being configured to move in response to movement of the slave joint; and an articulation actuation system that is coupled to the master joint and configured to act directly on the master joint without directly acting on the slave joint to move the master joint in at least one plane;

wherein the master and slave joints are operably coupled to each other such that movement of the master joint causes parallel movement of the slave joint while maintaining a position of the longitudinal axis of the central body of the tool shaft to thereby effect articulation of the end effector in at least one plane about the central body of the tool shaft.

2. The system of claim 1, wherein the tool shaft includes circumferentially spaced flexible tendons, and wherein the flexible tendons longitudinally extend along a length of the tool shaft, the length extending from a proximal-most end of the master joint to the distal-most end of the slave joint.

3. The system of claim 1, further comprising a shaft roll actuation system that is coupled to the tool shaft and is configured to rotate the tool shaft relative to the motor housing and the electromechanical arm.

4. The system of claim 1, further comprising an instrument roll actuation system that is coupled to the motor housing and is configured to rotate the tool shaft and a motor chassis within the motor housing simultaneously relative to the electromechanical arm.

5. The system of claim 1, wherein movement in the at least one plane is at least one of pitch and yaw.

6. The system of claim 1, wherein movement of the master joint in a first plane of the at least one plane is pitch and movement of the master joint in a second plane of the at least one plane is yaw.

7. The system of claim 1, wherein the articulation actuation system comprises a plurality of lever arms positioned at the proximal end of the master joint, each lever arm being configured to move the master joint in a respective one direction within the at least one plane.

8. The system of claim 1, wherein the articulation actuation system comprises at least one gear that is operatively coupled to the master joint and configured to control movement of the master joint.

9. The system of claim 8, wherein the articulation actuation system comprises at least one pulley assembly having at least one pulley and respective cable, and wherein the at least one pulley assembly is configured to cause rotation of the at least one gear to thereby cause articulation of the master joint in the at least one plane.

10. The system of claim 8, wherein the articulation actuation system comprises at least one lead screw that is coupled to the at least one gear and configured to cause rotational movement of the at least one gear to thereby cause articulation of the master joint in the at least one direction.

11. The system of claim 1, wherein the motor housing is configured to be removably coupled to the electromechanical arm.

12. The system of claim 1, wherein the master joint and the slave joint are each a continuum joint.

\* \* \* \* \*